(12) United States Patent
Buras et al.

(10) Patent No.: US 11,017,695 B2
(45) Date of Patent: May 25, 2021

(54) METHOD FOR DEVELOPING A MACHINE LEARNING MODEL OF A NEURAL NETWORK FOR CLASSIFYING MEDICAL IMAGES

(71) Applicant: Tienovix, LLC, Houston, TX (US)

(72) Inventors: William R. Buras, Friendswood, TX (US); Craig S. Russell, League City, TX (US); Kyle Q. Nguyen, League City, TX (US)

(73) Assignee: Tienovix, LLC, Houston, TX (US)

(*) Notice: Subject to any disclaimer, the term of this patent is extended or adjusted under 35 U.S.C. 154(b) by 0 days.

(21) Appl. No.: 16/727,844

(22) Filed: Dec. 26, 2019

(65) Prior Publication Data

US 2020/0286405 A1 Sep. 10, 2020

Related U.S. Application Data

(63) Continuation of application No. 15/878,314, filed on Jan. 23, 2018, now Pat. No. 10,636,323.
(Continued)

(51) Int. Cl.
*G09B 23/28* (2006.01)
*G06N 20/00* (2019.01)
(Continued)

(52) U.S. Cl.
CPC .............. *G09B 23/286* (2013.01); *A61B 8/06* (2013.01); *A61B 8/085* (2013.01); *A61B 8/4245* (2013.01);
(Continued)

(58) Field of Classification Search
CPC ....... G09B 23/28; G09B 23/286; G09B 23/30
(Continued)

(56) References Cited

U.S. PATENT DOCUMENTS

| 4,237,902 A | 12/1980 | Okazaki |
| 4,444,197 A | 4/1984 | Koyano et al. |

(Continued)

FOREIGN PATENT DOCUMENTS

| EP | 2807978 A1 | 12/2014 |
| WO | 2015150932 A1 | 10/2015 |

(Continued)

OTHER PUBLICATIONS

Ali, Murtaza et al., Signal Processing Overview of Ultrasound Systems for Medical Imaging, Texas Instruments, White Paper, SPRABI2, Nov. 2008, 27 pages.
(Continued)

*Primary Examiner* — Kurt Fernstrom
(74) *Attorney, Agent, or Firm* — Timothy L. Scott

(57) ABSTRACT

Methods for developing a machine learning model of a neural network for classifying medical images using a medical imaging system such as an ultrasound system. The methods involve capturing images during a first medical procedure, analyzing the images for the presence of one or more features, labeling the images as belonging to one or more classes, splitting the labeled images into a training set and a validation set. Training and validation processes are then performed, and the machine learning model may be used when training process metrics and validation process metrics for the training and validation processes are within acceptable thresholds.

20 Claims, 14 Drawing Sheets

Related U.S. Application Data

(60) Provisional application No. 62/450,051, filed on Jan. 24, 2017.

(51) Int. Cl.

| | | |
|---|---|---|
| *A61B 34/20* | (2016.01) | |
| *G16H 40/63* | (2018.01) | |
| *A61B 8/06* | (2006.01) | |
| *A61B 8/08* | (2006.01) | |
| *A61B 8/00* | (2006.01) | |
| *A61B 90/00* | (2016.01) | |
| *G16H 30/20* | (2018.01) | |
| *G06F 3/01* | (2006.01) | |
| *G09B 5/06* | (2006.01) | |
| *G02B 27/01* | (2006.01) | |

(52) U.S. Cl.
CPC .......... *A61B 8/4254* (2013.01); *A61B 8/4263* (2013.01); *A61B 8/466* (2013.01); *A61B 8/467* (2013.01); *A61B 8/52* (2013.01); *A61B 34/20* (2016.02); *A61B 90/361* (2016.02); *G06F 3/011* (2013.01); *G06F 3/016* (2013.01); *G06N 20/00* (2019.01); *G09B 5/065* (2013.01); *G16H 30/20* (2018.01); *G16H 40/63* (2018.01); *A61B 2034/2048* (2016.02); *A61B 2034/2055* (2016.02); *A61B 2090/365* (2016.02); *A61B 2090/378* (2016.02); *A61B 2090/3945* (2016.02); *A61B 2562/0219* (2013.01); *G02B 27/017* (2013.01)

(58) Field of Classification Search
USPC .................. 434/262, 267, 268, 272; 600/424
See application file for complete search history.

(56) References Cited

U.S. PATENT DOCUMENTS

| | | | |
|---|---|---|---|
| 5,906,578 A | 5/1999 | Rajan et al. | |
| 6,014,580 A | 1/2000 | Blume et al. | |
| 6,314,165 B1 | 11/2001 | Junqua et al. | |
| 6,929,481 B1 | 8/2005 | Alexander et al. | |
| 7,074,185 B2 | 7/2006 | Takeuchi | |
| 7,162,054 B2* | 1/2007 | Meisner | G01S 5/16 |
| | | | 348/169 |
| 7,219,997 B2 | 5/2007 | Yokota et al. | |
| 7,236,618 B1 | 6/2007 | Chui et al. | |
| 7,747,311 B2 | 6/2010 | Quaid | |
| 8,500,451 B2* | 8/2013 | Bronstein | G06F 19/3481 |
| | | | 434/262 |
| 8,992,230 B2* | 3/2015 | Tuchschmid | G09B 23/28 |
| | | | 434/262 |
| 10,636,323 B2* | 4/2020 | Buras | A61B 34/20 |
| 10,796,605 B2 | 10/2020 | Buras et al. | |
| 10,818,199 B2 | 10/2020 | Buras et al. | |
| 2003/0192557 A1 | 10/2003 | Krag et al. | |
| 2004/0019270 A1* | 1/2004 | Takeuchi | G06F 19/321 |
| | | | 600/407 |
| 2005/0216243 A1* | 9/2005 | Graham | G16H 50/50 |
| | | | 703/11 |
| 2009/0036775 A1* | 2/2009 | Ikuma | A61B 5/065 |
| | | | 600/443 |
| 2011/0306025 A1* | 12/2011 | Sheehan | A61B 8/4245 |
| | | | 434/267 |
| 2012/0035868 A1 | 2/2012 | Roche et al. | |
| 2012/0116221 A1* | 5/2012 | Sehgal | A61N 7/00 |
| | | | 600/439 |
| 2012/0178069 A1* | 7/2012 | McKenzie | G16H 50/50 |
| | | | 434/262 |
| 2013/0137076 A1 | 5/2013 | Perez et al. | |
| 2013/0237811 A1* | 9/2013 | Mihailescu | A61B 8/4438 |
| | | | 600/424 |
| 2013/0302768 A1 | 11/2013 | Webb | |
| 2014/0178843 A1 | 6/2014 | Smyth | |
| 2014/0199672 A1 | 7/2014 | Davidson | |
| 2014/0234814 A1 | 8/2014 | Krosky et al. | |
| 2014/0287393 A1* | 9/2014 | Kumar | A61B 34/35 |
| | | | 434/262 |
| 2014/0323863 A1* | 10/2014 | Azhari | A61B 8/15 |
| | | | 600/439 |
| 2015/0044654 A1* | 2/2015 | Lendvay | G09B 23/28 |
| | | | 434/262 |
| 2015/0125835 A1 | 5/2015 | Wittich et al. | |
| 2015/0254555 A1 | 9/2015 | Williams, Jr. et al. | |
| 2015/0261922 A1 | 9/2015 | Nawana et al. | |
| 2016/0093050 A1 | 3/2016 | Kim et al. | |
| 2016/0110871 A1 | 4/2016 | Kang et al. | |
| 2016/0157832 A1* | 6/2016 | Kang | A61B 8/5223 |
| | | | 600/443 |
| 2016/0174934 A1* | 6/2016 | Cong | A61B 8/08 |
| | | | 600/459 |
| 2016/0314715 A1 | 10/2016 | Savitsky | |
| 2017/0262982 A1* | 9/2017 | Pagoulatos | G06T 7/0012 |
| 2017/0360403 A1 | 12/2017 | Rothberg et al. | |
| 2017/0360411 A1* | 12/2017 | Rothberg | G06K 9/00912 |
| 2018/0153505 A1* | 6/2018 | Cadieu | A61B 34/20 |
| 2020/0211420 A1 | 7/2020 | Buras et al. | |
| 2020/0265745 A1 | 8/2020 | Buras et al. | |
| 2020/0265754 A1 | 8/2020 | Buras et al. | |
| 2020/0268349 A1 | 8/2020 | Buras et al. | |
| 2020/0286404 A1 | 9/2020 | Buras et al. | |

FOREIGN PATENT DOCUMENTS

| | | |
|---|---|---|
| WO | 2016040376 A1 | 3/2016 |
| WO | 2018140415 A1 | 8/2018 |

OTHER PUBLICATIONS

Basoglu, Chris et al., "CTNK Evaluate Image Transforms," available at https://docs.microsoft.com/en-us/cognitive-toolkit/archive/cntk-evaluate-image-transforms, Microsoft Corp., Redmond, Wasington, USA, Jul. 30, 2019.

Condino, Sara et al., "How to Build a Patient-Specific Hybrid Simulator for Orthopaedic Open Surgery: Benefits and Limits for Mixed-Reality Using Microsoft HoloLens," Journal of Healthcare Engineering vol. 2018, Article ID 5435097, 12 pages.

Cross Entropy. (n.d.). In Wikipedia. Retrieved Jan. 28, 2019 from https://en.wikipedia.org/wiki/Cross_entropy.

Eberhart, R.C. et al., "A New Optimizer Using Particle Swarm Theory," In: micro machine and human science, 1995. MHS '95, Proceedings of the Sixth International Symposium on Micro Machine and Human Science, 1995, pp. 39-43.

El Gamal et al., "Current trends in medical image registration and fusion," Egyptian Information Journal (2016) 17, 99-124, Oct. 21, 2015.

El-Seoud, Samir A. et al., " An Interactive Mixed Reality RayTracing Rendering Mobile Application of Medical Data in Minimally Invasive Surgeries," International Journal of Online Engineering, vol. 15, No. 6, 2019.

Frantz, Taylor et al., "Augmenting Microsoft's HoloLens with Vuforia Tracking for Neuronavigation", Healthcare Technology Letters, vol. 5, Issue 5, 2018, pp. 221-225.

He, Kaiming et al., "Deep Residual Learning for Image Recognition," The IEEE Conference on Computer Vision and Pattern Recognition (CVPR), 2016, pp. 770-778.

Kobayashi, Leo et al., " Exploratory Application of Augmented Reality/Mized Reality Devices for Acute Care Procedure Training," Educational Advances, Dec. 14, 2017.

Kranen, Philipp et al., "Object Detection Using Fas R-CNN," online document available at https://docs.microsoft. com/en-us/cognitive-toolkit/object-detection-using-fast+cnn-brainscript#map-mean-average-precision, Microsoft Corp., Redmond, Washington, USA, Aug. 29, 2017 (n. p., see "mAP. (mean Average Precision)").

Kress, Bernard, "Optical design of next-gen augmented reality," Electra Optics, Feb. 2019.

(56) References Cited

OTHER PUBLICATIONS

Kumar, Anirudh et al., "Plaque Volume of Carotid Endarterectomy Specimens Measured by 3D Ultrasound Technology," JACC: CardioVascular Imaging, vol. 9, No. 9, Sep. 2016, pp. 1118-1119.
Lee, Min Woo et al., "Percutaneous Radiofrequency Ablation of Hepatocellular Carcinoma: Fusion Imaging Guidance for Management of Lesions with Poor Conspicuity at Conventional Sonography", American Journal of Roentgenology, No. 198, Jun. 2012, pp. 1438-1444.
Magee D. et al. "An augmented reality simulator for ultrasound guided needle placement training" Medical Biological Engineering Computing (2007) 45:957-967, Published Jul. 26, 2007, DOI 10.1007/s11517-007-0231-9.
Mahvash, Mehran et al., " A novel augmented reality system of image projection for image-guided neurosurgery," Acta Neurochirurgica (2013) 155:943-947 DOI 10.1007/s00701-013-1668-2, Mar. 15, 2013.
Mather, Carey et al., "Helping Hands: Using Augmented Reality to Provide Remote Guidance to Health Professionals," Context Sensitive Health Informatics: Redesigning Healthcare Work, C. NØhr et al (Eds.), IOS Press.
McCaffrey, James , "Neural Networks Using C# Succinctly," Syncfusion, Inc., Morrisville, NJ (USA), pp. 11-13, 49-51, 70-80, 95-114.
"Neochord wins exclusive rights to new imagin tech," Medical Device Daily, Oct. 4, 2012 p. 3.
PCT Search Report & Written Opinion dated Aug. 2, 2018, International Application No. PCT/US2018/014922 filed Jan. 23, 2018.
Rizatto, Giorgio et al., "Breast Imaging and Volume Navigation: MR imaging and Ultrasound Conregistration," Ultrasound Clinics, vol. 4, No. 3, Elsevier, Jul. 2009, pp. 261-271.
"Simple Guide to Confusion Matrix Terminology," available at https://www.dataschool.io/simple-guide-to-confusion-matrix-terminology/, Data School, Mar. 25, 2014.
Samosky, Joseph T. et al., "Real-Time "X-Ray Vision" for Healthcare Simulation: An Iteractive Projective Overlay System to Enhance Intubation Training and Other Procedural Training," Medicine Meets Virtual Reality 18, J.D. Westwood et al. (Eds.) IOS Press 2011.
Von Bardeleben, Ralph Stephan et al., "First in human transcatheter COMBO mitral valve repair with direct ring annuloplasty and neochord leaflet implantation to treat degenerative mitral regurgitation: feasibility of the simultaneous toolbox concept guided by 3D echo and computed tomography fusion imaging," Cardiovascular Flashlight doi:10.1093/eurheartj/ehx595, Oct. 2017, p. 1314.
Wang, A. et al., "Fusion and visualization of intraoperative cortical images with preoperative models for epilepsy surgical planning and guidance," Computer Aided Surgery, Jul. 2011, 16(4): 149-160.
Wang, Shen-Yung, "Real-Time Fusion Imaging of Liver Ultrasound," Journal of Medical Ultrasound (2017) 25, 9-11, Mar. 27, 2017.
Wang, Shiyao et al., "Augmented Reality as a Telemedicine Plattorm for Remote Procedural Training," Sensors 2017, 17, 2294; doi:10.3390/s17102294.
Wang, Xiang et al., "Precise 3D/2D calibration between a RGB-D sensor and a C-arm fluoroscope," International Journal of Computer Assisted Radiology & Surgery (2016). 11:1385-1395, Jan. 25, 2016.
Wilson, Kenneth L. et al., "Using Augmented Reality as a Clinical Support Tool to Assist Combat Medics in the Treatment of Tension Pneumothoraces," Military Medicine, 178, 9:981, 2013.
Wu, Ming-Long et al., "An Augmented Reality System Using Improved-Iterative Closest Point Algorithm for On-Patient Medical Image Visualization," Sensors 2018, 18, 2505;doi:10.3390/s18082505, Aug. 1, 2018.
Yang, Eric et al. "Real-Time Co-Registration Using Naval Ultrasound Technology: Ex Vivo Validation and In Vivo Applications," Journal of the American Society of Echocardiography, vol. 24, No. 7, Jul. 2011, pp. 720-728.
Office Action dated Mar. 16, 2020, U.S. Appl. No. 16/732,353, filed Jan. 1, 2020.
Final Office Action dated Apr. 13, 2020, U.S. Appl. No. 16/732,353, filed Jan. 1, 2020.
Corrected Notice of Allowability dated Aug. 10, 2020, U.S. Appl. No. 16/732,353, filed Jan. 1, 2020.
Notice of Allowance dated Jun. 22, 2020, U.S. Appl. No. 16/732,353, filed Jan. 1, 2020.
Office Action dated Jan. 3, 2020, U.S. Appl. No. 15/878,314, filed Jan. 23, 2018.
Notice of Allowance dated Mar. 12, 2020, U.S. Appl. No. 15/878,314, filed Jan. 23, 2018.
Communication Pursuant to Article 94(3) EPC dated Jul. 8, 2020, European Patent Application No. 18704666.9 filed Jan. 23, 2018.
Notice of Allowance dated Dec. 9, 2020, U.S. Appl. No. 16/727,824, filed Dec. 26, 2019.
Notice of Allowance dated Jul. 27, 2020, U.S. Appl. No. 16/727,840, filed Dec. 26, 2019.
Office Action dated Mar. 12, 2020, U.S. Appl. No. 16/727,840, filed Dec. 26, 2019.
Final Office Action dated Jun. 30, 2020, U.S. Appl. No. 16/727,840, filed Dec. 26, 2019.
Notice of Allowance dated Mar. 10, 2021, U.S. Appl. No. 16/727,832, filed Dec. 26, 2019.
Notice of Allowance dated Dec. 2, 2020, U.S. Appl. No. 16/727,832, filed Dec. 26, 2019.
Office Action dated Jul. 10, 2020, U.S. Appl. No. 16/727,832, filed Dec. 26, 2019.
Notice of Allowance dated Mar. 23, 2021, U.S. Appl. No. 16/727,824, filed Dec. 26, 2019.
Office Action dated Jul. 10, 2020, U.S. Appl. No. 16/727,824, filed Dec. 26, 2019.

\* cited by examiner

METHOD FOR DEVELOPING A MACHINE LEARNING MODEL OF A NEURAL NETWORK FOR CLASSIFYING MEDICAL IMAGES

CROSS-REFERENCE TO RELATED APPLICATIONS

This application claims the benefit of priority to U.S. patent application Ser. No. 15/878,314, now U.S. Pat. No. 10,636,323, filed on Jan. 23, 2018, and to U.S. Provisional Application No. 62/450,051, filed on Jan. 24, 2017, both of which are hereby incorporated by reference herein in their entirety.

STATEMENT REGARDING GOVERNMENT SUPPORT

This invention was made with Government support under contract NNX16CC52 awarded by NASA. The Government has certain rights in this invention.

BACKGROUND OF THE INVENTION

The present disclosure relates to systems for providing improved training and guidance to equipment users, and more particularly systems and methods for providing real-time, three-dimensional (3D) augmented reality (AR) feedback-based guidance in the use of medical equipment by novice users, to achieve improved diagnostic or treatment outcomes.

In many medical situations, diagnostic or treatment of medical conditions, which may include life-saving care, must be provided by persons without extensive medical training. This may occur because trained personnel are either not present or are unable to respond. For example, temporary treatment of broken bones occurring in remote wilderness areas must often be provided by a companion of the injured patient, or in some cases as self-treatment by the patient alone. The need for improved medical treatment in remote or extreme situations has led to Wilderness First Aid training courses for hikers and backpackers. Battlefield injuries such as gunshot or blast injuries often require immediate treatment, e.g., within minutes or even seconds, by untrained personnel under extreme conditions to stabilize the patient until transport is available. Injuries to maritime personnel may occur on smaller vessels lacking a full-time physician or nurse, and illness or injuries may require treatment by persons with little or no training. Similarly, injuries or illnesses occurring to persons in space (e.g., the International Space Station) may also require treatment by persons with limited or incomplete medical training.

In many instances, such as maritime vessels and injuries in space, adequate medical equipment may be available, but the efficacy of the use of the equipment may be limited by the training level of the caregiver(s). Improved treatment or diagnostic outcomes may be available if improved training is available to caregivers having limited medical training. As used herein, caregivers having little or no medical training for the use of a particular medical device or medical technology are referred to as "novice users" of the technology. Novice users may include persons having a rudimentary or working knowledge of a medical device or technology, but less than an expert or credentialed technician for such technology.

The present invention provides systems and methods for guiding medical equipment users, including novice users. In some embodiments, systems of the present disclosure provide real-time guidance to a medical equipment user. In some embodiments, systems disclosed herein provide three-dimensional (3D) augmented-reality (AR) guidance to a medical device user. In some embodiments, systems of the present disclosure provide machine learning guidance to a medical device user. Guidance systems disclosed herein may provide improved diagnostic or treatment results for novice users of medical devices. Use of systems of the present invention may assist novice users to achieve results comparable to those obtained by expert or credentialed medical caregivers for a particular medical device or technology.

Although systems of the present invention may be described for particular medical devices and medical device systems, persons of skill in the art having the benefit of the present disclosure will appreciate that these systems may be used in connection with other medical devices not specifically noted herein. Further, it will also be appreciated that systems according to the present invention not involving medical applications are also within the scope of the present invention. For example, systems of the present invention may be used in many industrial or commercial settings to train users to operate may different kinds of equipment, including heavy machinery as well as many types of precision instruments, tools, or devices. Accordingly, the particular embodiments disclosed above are illustrative only, as the invention may be modified and practiced in different but equivalent manners apparent to those skilled in the art having the benefit of the teachings herein. Examples, where provided, are all intended to be non-limiting. Furthermore, exemplary details of construction or design herein shown are not intended to limit or preclude other designs achieving the same function. The particular embodiments disclosed above may be altered or modified and all such variations are considered within the scope and spirit of the invention, which are limited only by the scope of the claims.

Many future manned spaceflight missions (e.g., by NASA, the European Space Agency, or non-governmental entities) will require medical diagnosis and treatment capabilities that address the anticipated health risks and also perform well in austere, remote operational environments. Spaceflight-ready medical equipment or devices will need to be capable of an increased degree of autonomous operation, allowing the acquisition of clinically relevant and diagnosable data by every astronaut, not just select physician crew members credentialed in spaceflight medicine.

Augmented reality systems have been developed that provide step-by-step instructions to a user in performing a task. Such prior art systems may provide a virtual manual or virtual checklist for a particular task (e.g., performing a repair or maintenance procedure). In some systems, the checklist may be visible to the user via an augmented reality (AR) user interface such as a headset worn by the user. Providing the user with step-by-step instructions or guidance may reduce the need for training for a wide variety of tasks, for example, by breaking a complex task into a series of simpler steps. In some instances, context-sensitive animations may be provided through an AR user interface in the real-world workspace. Existing systems, however, may be unable to guide users in delicate or highly specific tasks that are technique-sensitive, such as many medical procedures or other equipment requiring a high degree of training for proficiency.

Thus, there is a need for AR systems capable of guiding a novice user of equipment in real time through a wide range of unfamiliar tasks in remote environments such as space or remote wilderness (e.g., arctic) conditions. These may include daily checklist items (e.g., habitat systems procedures and general equipment maintenance), assembly and testing of complex electronics setups, and diagnostic and interventional medical procedures. AR guidance systems desirably would allow novice users to be capable of autonomously using medical and other equipment or devices with a high degree of procedural competence, even where the outcome is technique-sensitive.

SUMMARY

In one embodiment, the present invention comprises a medical guidance system (100) for providing real-time, three-dimensional (3D) augmented reality (AR) feedback guidance in the use of a medical equipment system (200), the medical guidance system comprising: a medical equipment interface to a medical equipment system (200), wherein said medical equipment interface is capable of receiving data from the medical equipment system during a medical procedure performed by a user; an augmented reality user interface (ARUI) (300) for presenting data pertaining to both real and virtual objects to the user during at least a portion of the performance of the medical procedure; a three-dimensional guidance system (3DGS) (400) that is capable of sensing real-time user positioning data relating to one or more of the movement, position, and orientation of at least a portion of the medical equipment system (200) during said medical procedure performed by the user; a library (500) containing 1) stored reference positioning data relating to one or more of the movement, position, and orientation of at least a portion of the medical equipment system (200) during a reference medical procedure and 2) stored reference outcome data relating to an outcome of said reference medical procedure; and a machine learning module (MLM) (600) for providing at least one of 1) position-based 3D AR feedback to the user based on the sensed user positioning data and the reference positioning data, and 2) outcome-based 3D AR feedback to the user based on data received from the medical equipment system during the medical procedure performed by the user and reference outcome data.

In one embodiment, the present invention comprises a medical guidance system (100) for providing real-time, three-dimensional (3D) augmented reality (AR) feedback guidance in the use of a medical equipment system (200), the medical guidance system comprising: a computer 700 comprising a medical equipment interface to a medical equipment system (200), wherein said medical equipment interface receives data from the medical equipment system during a medical procedure performed by a user to achieve a medical procedure outcome; an AR interface to an AR head mounted display (HMD) for presenting information pertaining to both real and virtual objects to the user during the performance of the medical procedure; a guidance system interface (GSI) to a three-dimensional guidance system (3DGS) (400) that senses real-time user positioning data relating to one or more of the movement, position, and orientation of at least a portion of the medical equipment system (200) within a volume of a user's environment during a medical procedure performed by the user; a library (500) containing 1) stored reference positioning data relating to one or more of the movement, position, and orientation of at least a portion of the medical equipment system (200) during a reference medical procedure and 2) stored reference outcome data relating to an outcome of a reference performance of the reference medical procedure; and a machine learning module (MLM) (600) for providing at least one of 1) position-based 3D AR feedback to the user based on the sensed user positioning data and 2) outcome-based 3D AR feedback to the user based on the medical procedure outcome, the MLM (600) comprising a position-based feedback module comprising a first module for receiving and analyzing real-time user positioning data; a second module for comparing the user positioning data to the stored reference positioning data, and a third module for generating real-time position-based 3D AR feedback based on the output of the second module, and providing said real-time position-based 3D AR feedback to the user via the ARUI (300); and an outcome-based feedback module comprising a fourth module for receiving real-time data from the medical equipment system (200) via said medical equipment interface as the user performs the medical procedure; a fifth module for comparing the real-time data received from the medical equipment system (200) as the user performs the medical procedure to the stored reference outcome data, and a sixth module for generating real-time outcome-based 3D AR feedback based on the output of the fifth module, and providing said real-time outcome-based 3D AR feedback to the user via the ARUI (300).

In one embodiment, the present invention comprises a method for providing real-time, three-dimensional (3D) augmented reality (AR) feedback guidance to a user of a medical equipment system, the method comprising: receiving data from a medical equipment system during a medical procedure performed by a user of the medical equipment to achieve a medical procedure outcome; sensing real-time user positioning data relating to one or more of the movement, position, and orientation of at least a portion of the medical equipment system within a volume of the user's environment during the medical procedure performed by the user; retrieving from a library at least one of 1) stored reference positioning data relating to one or more of the movement, position, and orientation of at least a portion of the medical equipment system during reference a medical procedure, and 2) stored reference outcome data relating to a reference performance of the medical procedure; comparing at least one of 1) the sensed real-time user positioning data to the retrieved reference positioning data, and 2) the data received from the medical equipment system during a medical procedure performed by the user to the retrieved reference outcome data; generating at least one of 1) real-time position-based 3D AR feedback based on the comparison of the sensed real-time user positioning data to the retrieved reference positioning data, and 2) real-time outcome-based 3D AR feedback based on the comparison of the data received from the medical equipment system during a medical procedure performed by the user to the retrieved reference outcome data; and providing at least one of the real-time position-based 3D AR feedback and the real-time outcome-based 3D AR feedback to the user via an augmented reality user interface (ARUI).

In one embodiment, the present invention comprises a method for developing a machine learning model of a neural network for classifying images for a medical procedure using an ultrasound system, the method comprising: A) performing a first medical procedure using an ultrasound system; B) automatically capturing a plurality of ultrasound images during the performance of the first medical procedure, wherein each of the plurality of ultrasound images is captured at a defined sampling rate according to defined image capture criteria; C) providing a plurality of feature modules, wherein each feature module defines a feature which may be present in an image captured during the medical procedure; D) automatically analyzing each image using the plurality of feature modules; E) automatically determining, for each image, whether or not each of the plurality of features is present in the image, based on the analysis of each imagine using the feature modules; F) automatically labeling each image as belonging to one class of a plurality of image classes associated with the medical procedure; G) automatically splitting the plurality of images into a training set of images and a validation set of images; H) providing a deep machine learning (DML) platform having a neural network to be trained loaded thereon, the DML platform having a plurality of adjustable parameters for controlling the outcome of a training process; I) feeding the training set of images into the DML platform; J) performing the training process for the neural network to generate a machine learning model of the neural network; K) obtaining training process metrics of the ability of the generated machine learning model to classify images during the training process, wherein the training process metrics comprise at least one of a loss metric, an accuracy metric, and an error metric for the training process; L) determining whether each of the at least one training process metrics is within an acceptable threshold for each training process metric; M) if one or more of the training process metrics are not within an acceptable threshold, adjusting one or more of the plurality of adjustable DML parameters and repeating steps J, K, and L; N) if each of the training process metrics is within an acceptable threshold for each metric, performing a validation process using the validation set of images; O) obtaining validation process metrics of the ability of the generated machine learning model to classify images during the validation process, wherein the validation process metrics comprise at least one of a loss metric, an accuracy metric, and an error metric for the validation process; P) determining whether each of the validation process metrics is within an acceptable threshold for each validation process metric; Q) if one or more of the validation process metrics are not within an acceptable threshold, adjusting one or more of the plurality of adjustable DML parameters and repeating steps J-P; and R) if each of the validation process metrics is within an acceptable threshold for each metric, storing the machine learning model for the neural network.

DESCRIPTION

Figure 1:
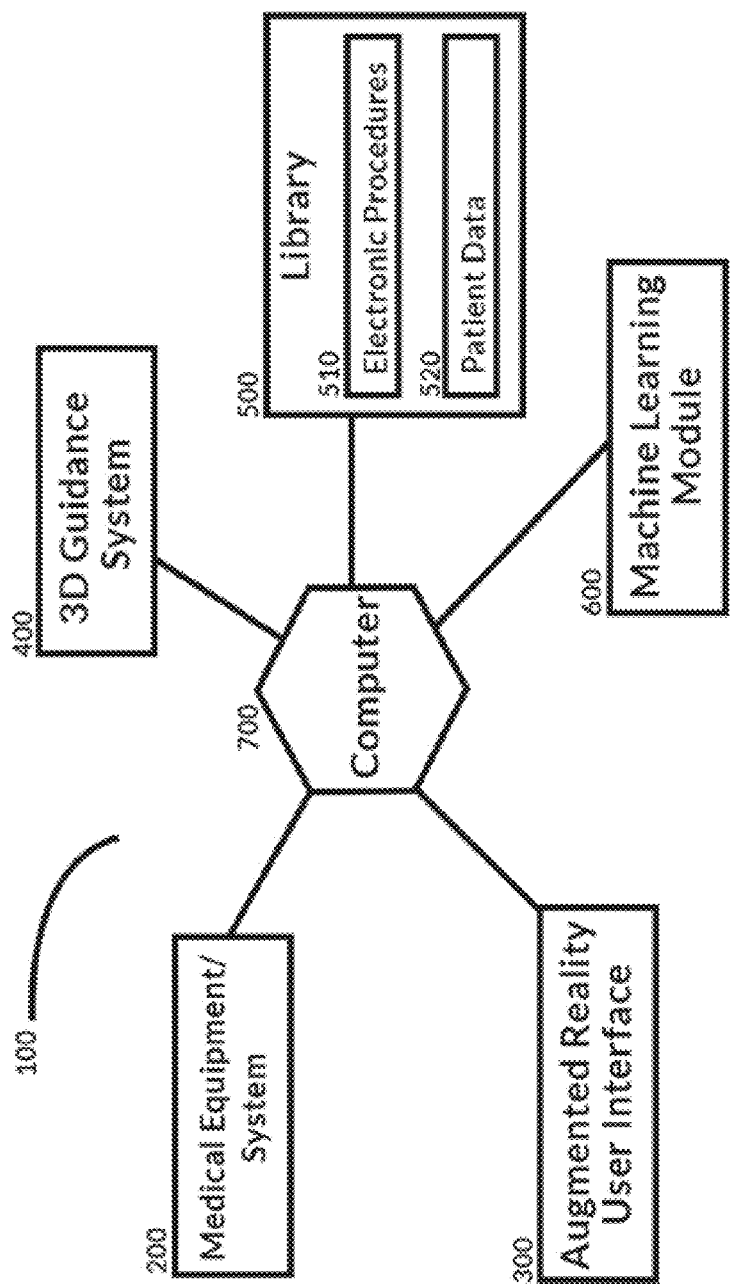
FIG. 1 is a block diagram view of a system for providing real-time, three-dimensional (3D) augmented reality (AR) guidance in the use of a medical device system.

Exemplary embodiments are illustrated in referenced figures of the drawings. The embodiments disclosed herein are considered illustrative rather than restrictive. No limitation on the scope of the technology and on the claims that follow is to be imputed to the examples shown in the drawings and discussed here.

As used herein, the term "augmented reality" refers to display systems or devices capable of allowing a user to sense (e.g., visualize) objects in reality (e.g., a patient on an examination table and a portion of a medical device used to examine the patient), as well as objects that are not present in reality but which relate in some way to objects in reality, but which are displayed or otherwise provided in a sensory manner (e.g., visually or via sound) in the AR device. Augmented reality as used herein is a live view of a physical, real-world environment that is augmented to a user by computer-generated perceptual information that may include visual, auditory, haptic (or tactile), somatosensory, or olfactory components. The augmented perceptual information is overlaid onto the physical environment in spatial registration so as to be perceived as immersed in the real world. Thus, for example, augmented visual information is displayed relative to one or more physical objects in the real world, and augmented sounds are perceived as coming from a particular source or area of the real world. This could include, as nonlimiting examples, visual distance markers between particular real objects in the AR display, or grid lines allowing the user to gauge depth and contour in the visual space, and sounds, odors, and tactile inputs highlighting or relating to real objects.

A well-known example of AR devices are heads-up displays on military aircraft and some automobiles, which allow the pilot or driver to perceive elements in reality (the landscape and/or aerial environment) as well as information related to the environment (e.g., virtual horizon and plane attitude/angle, markers for the position of other aircraft or targets, etc.) that is not present in reality but which is overlaid on the real environment. The term "augmented reality" (AR) is intended to distinguish systems herein from "virtual reality" (VR) systems that display only items that are not actually present in the user's field of view. Examples of virtual reality systems include VR goggles for gaming that present information to the viewer while blocking entirely the viewer's perception of the immediate surroundings, as well as the display on a television screen of the well-known "line of scrimmage" and "first down" markers in football games. While the football field actually exists, it is not in front of the viewer; both the field and the markers are only presented to the viewer on the television screen.

In one aspect of the present disclosure, a 3D AR system according to the present disclosure may be provided to a novice medical device user for real-time, three-dimensional guidance in the use of an ultrasound system. Ultrasound is a well-known medical diagnostic and treatment technology currently used on the International Space Station (ISS) and planned for use in future deep-space missions. A variety of ultrasound systems may be used in embodiments herein. In one nonlimiting example, the ultrasound system by be the Flexible Ultrasound System (FUS), an ultrasound platform being developed by NASA and research partners for use in space operations.

FIG. 1 is a block diagram view of one embodiment of a system for providing real-time, three-dimensional (3D) augmented reality (AR) guidance in the use of medical equipment by novice users having limited medical training, to achieve improved diagnostic or treatment outcomes. The system includes a computer 700 in communication with additional system components. Although FIG. 1 is a simplified illustration of one embodiment of a 3D AR guidance system 100, computer 700 includes various interfaces (not shown) to facilitate the transfer and receipt of commands and data with the other system components. The interfaces in computer 700 may comprise software, firmware, hardware or combinations thereof.

In one embodiment, computer 700 interfaces with a medical equipment system 200, which in one embodiment may be an ultrasound system. In other embodiments, different medical equipment, devices or systems may be used instead of or in addition to ultrasound systems. In the embodiment depicted in FIG. 1, the medical equipment system 200 is included as part of the 3D AR guidance system 100. In one embodiment, the medical equipment system 200 is not part of the guidance system 100; instead, guidance system 100 includes a medical equipment system interface (MESI) to communicate with the medical equipment system 200, which may comprise any of a variety of available medical device systems in a "plug-and-play" manner.

In one embodiment, the 3D AR guidance system 100 also includes an augmented reality user interface (ARUI) 300. The ARUI 300 may comprise a visor having a viewing element (e.g., a viewscreen, viewing shield or viewing glasses) that is partially transparent to allow a medical equipment user to visualize a workspace (e.g., an examination room, table or portion thereof). In one embodiment, the ARUI 300 includes a screen upon which virtual objects or information can be displayed to aid a medical equipment user in real-time (i.e., with minimal delay between the action of a novice user and the AR feedback to the action, preferably less than 2 seconds, more preferably less than 1 second, most preferably 100 milliseconds or less). As used herein, three-dimensional (3D) AR feedback refers to augmented reality sensory information (e.g., visual or auditory information) providing to the user based at least in part on the actions of the user, and which is in spatial registration with real world objects perceptible (e.g., observable) to the user. The ARUI 300 provides the user with the capability of seeing all or portions of both real space and virtual information overlaid on or in registration with real objects visible through the viewing element. The ARUI 300 overlays or displays (and otherwise presents, e.g., as sounds or tactile signals) the virtual information to the medical equipment user in real time. In one embodiment, system also includes an ARUI interface (not shown) to facilitate communication between the headset and the computer 700. The interface may be located in computer 700 or ARUI 300, and may comprise software, firmware, hardware, or combinations thereof.

A number of commercially available AR headsets may be used in embodiments of the present invention. The ARUI 300 may include one of these commercially available headsets. In the embodiment depicted in FIG. 1, the ARUI is included as part of the 3D AR guidance system 100. In an alternative embodiment, the ARUI 300 is not part of the guidance system 100, and guidance system 100 instead includes an ARUI interface, which may be provided as software, firmware, hardware or a combination thereof in computer 700. In this alternative embodiment, the ARUI interface communicates with the ARUI 300 and one or more other system components (e.g., computer 700), and ARUI 300 may comprise any of above-described commercially available headsets in a "plug-and-play" manner.

The embodiment of FIG. 1 further comprises a three-dimensional guidance system (3DGS) 400 that senses or measures real objects in real-time within a volume in the user's environment. The 3DGS 400 is used to map virtual information onto the real objects for display or other sensory presentation to the user via the ARUI 300. Although a variety of different kinds of three-dimensional guidance systems may be used in various embodiments, all such systems 400 determine the position of one or more objects, such as a moveable sensor, relative to a fixed transmitter within a defined operating volume. The 3DGS 400 additionally provides the positional data to one or more other modules in FIG. 1 (e.g., to the machine learning module 600) via computer 700.

In one embodiment, the 3DGS 400 senses real-time user positioning data while a novice user performs a medical procedure. User positioning data relates to or describes one or more of the movement, position, and orientation of at least a portion of the medical equipment system 200 while the user (e.g., a novice) of performs a medical procedure. User positioning data may, for example, include data defining the movement of an ultrasound probe during an ultrasound procedure performed by the user. User positioning data may be distinguished from user outcome data, which may be generated by medical equipment system 200 while the user performs a medical procedure, and which includes data or information indicating or pertaining to the outcome of a medical procedure performed by the user. User outcome data may include, as a nonlimiting example, a series of ultrasound images captured while the user performs an ultrasound procedure, or an auditory or graphical record of a patient's cardiac activity, respiratory activity, brain activity, etc.

In one embodiment, the 3DGS 400 is a magnetic GPS system such as VolNav, developed by GE, or other magnetic GPS system. Magnetic GPS tracking systems While magnetic GPS provides a robust, commercially available means of obtaining precision positional data in real-time, in some environments (e.g., the International Space Station) magnetic GPS may be unable to tolerate the small magnetic fields prevalent in such environments. Accordingly, in some embodiments, alternative or additional 3D guidance systems for determining the position of the patient, tracking the user's actions, or tracking one or more portions of the medical equipment system 200 (e.g., an ultrasound probe) may be used instead of a magnetic GPS system. These may include, without limitation, digital (optical) camera systems such as the DMA6SA and Optitrack systems, infrared cameras, and accelerometers and/or gyroscopes.

In the case of RGB (color) optical cameras and IR (infrared) depth camera systems, the position and rotation of the patient, the user's actions, and one or more portions of the medical equipment system may be tracked using non-invasive external passive visual markers or external active markers (i.e., a marker emitting or receiving a sensing signal) coupled to one or more of the patient, the user's hands, or portions of the medical equipment. The position and rotation of passive markers in the real world may be measured by the depth cameras in relation to a volume within the user's environment (e.g., an operating room volume), which may be captured by both the depth cameras and color cameras.

In the case of accelerometers and gyroscopes, the combination of acceleration and gyroscopes comprises inertial measurement units (IMUs), which can measure the motion of subjects in relation to a determined point of origin or reference plane, thereby allowing the position and rotation of subjects to be derived. In the case of a combination of color cameras, depth cameras, and IMUs, the aggregation of measured position and rotation data (collectively known as pose data) becomes more accurate.

In an alternative embodiment, the 3DGS 400 is not part of the guidance system 100, and guidance system 100 instead includes a 3DGS interface, which may be provided as software, firmware, hardware or a combination thereof in computer 700. In this alternative embodiment, the 3DGS interface communicates with the 3DGS 400 and one or more other system components (e.g., computer 700), and 3DGS 400 interfaces with the system 100 (e.g., via computer 700) in a "plug-and-play" manner.

In one embodiment of the invention, the 3DGS 400 tracks the user's movement of an ultrasound probe (provided as part of medical equipment system 200) relative to the body of the patient in a defined examination area or room. The path and position or orientation of the probe may be compared to a desired reference path and position/orientation (e.g., that of an expert user such as a physician or ultrasound technician during the examination of a particular or idealized patient for visualizing a specific body structure). This may include, for example, an examination path of an expert user for longitudinal or cross-sectional visualization of a carotid artery of a patient using the ultrasound probe.

Differences between the path and/or position/orientation of the probe during an examination performed by a novice user in real-time, and an idealized reference path or position/orientation (e.g., as taken during the same examination performed by an expert), may be used to provide real-time 3D AR feedback to the novice user via the ARUI 300. This feedback enables the novice user to correct mistakes or incorrect usage of the medical equipment and achieve an outcome similar to that of the expert user. The real-time 3D AR feedback may include visual information (e.g., a visual display of a desired path for the novice user to take with the probe, a change in the position or orientation of the probe, etc.), tactile information (e.g., vibrations or pulses when the novice user is in the correct or incorrect position), or sound (e.g., beeping when the novice user is in the correct or incorrect position).

Referring again to FIG. 1, system 100 further includes a library 500 of information relating to the use of the medical equipment system 200. The library 500 includes detailed information on the medical equipment system 200, which may include instructions (written, auditory, and/or visually) for performing one or more medical procedures using the medical equipment system, and reference information or data in the use of the system to enable a novice user to achieve optimal outcomes (i.e., similar to those of an expert user) for those procedures. In one embodiment, library 500 includes stored reference information relating to a reference performance (e.g., an expert performance) of one or more medical procedures. This may include one or both of stored reference positioning data, which relates to or describes one or more of the movement, position, and orientation of at least a portion of the medical equipment system 200 during a reference performance of a medical procedure, and stored reference outcome data, which includes data or information indicating or pertaining to a reference outcome of a medical procedure (e.g., when performed by an expert). Reference positioning data may include, as a nonlimiting example, data defining the reference movement of an ultrasound probe during a reference performance performing an ultrasound procedure. Reference outcome data may include, as a nonlimiting example, data comprising part or all of the outcome of a medical procedure, such as a series of ultrasound images capturing one or more desired target structures of a patient's body, or an auditory or graphical record of a patient's cardiac activity, respiratory activity, brain activity, etc. In some embodiments, the library 500 may include patient data, which may be either generic data relating to the use of the medical equipment system on a number of different patients, or patient-specific data (i.e., data relating to the use of the equipment system on one or more specific patients) to guide a user of the medical device to treat a specific patient. Additional information (e.g., user manuals, safety information, etc.) for the medical equipment system 200 may also be present in the library 500.

A machine learning module (MLM) 600 is provided to generate feedback to a novice user of the system 100, which may be displayed in the ARUI 300. MLM 600 is capable of comparing data of a novice user's performance of a procedure or task to that of a reference performance (e.g., by an expert user). MLM 600 may receive real-time data relating to one or both of 1) the movement, position or orientation ("positioning data") of a portion of the medical equipment 200 during the novice user's performance of a desired medical task (e.g., the motion, position and orientation of an ultrasound probe as manipulated by a novice user to examine a patient's carotid artery), and 2) data received from the medical equipment 200 relating to an outcome of the medical procedure ("outcome data").

As previously noted, the positioning data (e.g., relating to the real-time motion, position or orientation an ultrasound probe during use by a novice user) is obtained by the 3DGS 400, which senses the position and/or orientation of a portion of the medical device at a desired sampling rate (e.g., 100 times per second (Hz) up to 0.1 Hz or once every 10 seconds). The positioning data is then processed by one or more of the 3DGS 400, computer 700, or MLM 600 to determine the motion and position/orientation of a portion of the medical equipment system 200 as manipulated by the novice user during the medical procedure.

The MLM 600 includes a plurality of modules, which may comprise software, firmware or hardware, for generating and providing one or both of position-based and outcome-based feedback to user. In one embodiment, MLM 600 includes a first module for receiving and processing real-time user positioning data, a second module for comparing the real-time user positioning data (obtained by the 3DGS 400) to corresponding stored reference positioning data in patient library 500 of the motion and position/orientation obtained during a reference performance of the same medical procedure or task. Based on the comparison of the movements of the novice user and the reference performance, the MLM 600 may then determine discrepancies or variances of the performance of the novice user and the reference performance. A third module in the MLM generates real-time position-based 3D AR feedback based on the comparison performed by the second module, and provides the real-time position-based 3D AR feedback to the user via the ARUI 300. The real-time, 3D AR position-based feedback may include, for example, virtual prompts to the novice user to correct or improve the novice's user's physical performance (i.e., manipulation of the relevant portion of the medical equipment system 200) of the medical procedure or task. The feedback may include virtual still images, virtual video images, sounds, or tactile information. For example, the MLM 600 may cause the ARUI 300 to display a virtual image or video instructing the novice user to change the orientation of a probe to match a desired reference (e.g., expert) orientation, or may display a correct motion path to be taken by the novice user in repeating a prior reference motion, with color-coding to indicate portions of the novice user's prior path that were erroneous or sub-optimal. In some embodiments, the MLM 600 may cause the ARUI 300 to display only portions of the novice user's motion that must be corrected.

In one embodiment, the MLM 600 also includes a fourth module that receives real-time data from the medical equipment system 200 itself (e.g., via an interface with computer 700) during a medical procedure performed by the novice user, and a fifth module that compares that data to stored reference outcome data from library 500. For example, the MLM 600 may receive image data from an ultrasound machine during use by a novice user at a specified sampling rate (e.g., from 100 Hz to 0.1 Hz), or specific images captured manually by the novice user, and may compare the novice user image data to stored reference image data in library 500 obtained during a reference performance of the medical procedure (e.g., by an expert user such as an ultrasound technician).

The MLM 600 further includes a sixth module that generates real-time outcome-based feedback based on the comparison performed in the fifth module, and provides real-time, 3D AR outcome-based feedback to the user via the ARUI 300. The real-time outcome-based feedback may include virtual prompts to the user different from, or in addition to, the virtual prompts provided from the positioning data. Accordingly, the outcome data provided by MLM 600 may enable the novice user to further refine his or her use of the medical device, even when the positioning comparison discussed above indicates that the motion, position and/or orientation of the portion of the medical device manipulated by the novice user is correct. For example, the MLM 600 may use the outcome data from the medical device 200 and library 500 to cause the ARUI 300 to provide a virtual prompt instructing the novice user to press an ultrasound probe deeper or shallower into the tissue to the focus the ultrasound image on a desired target such as a carotid artery. The virtual prompt may comprise, for example, an auditory instruction or a visual prompt indicating the direction in which the novice user should move the ultrasound probe. The MLM 600 may also indicate to the novice user whether an acceptable and/or optimal outcome in the use of the device has been achieved.

It will be appreciated from the foregoing that MLM 600 can generate and cause ARUI 300 to provide virtual guidance based on two different types of feedback, including 1) position-based feedback based on the positioning data from the 3DGS 400 and 2) outcome-based feedback based on outcome data from the medical equipment system 200. In some embodiments the dual-feedback MLM 600 provides a tiered guidance to a novice user: the position-based feedback is used for high-level prompts to guide the novice user in performing the overall motion for a medical procedure, while the outcome-based feedback from the medical device 200 may provide more specific guidance for fine or small movements in performing the procedure. Thus, MLM 600 may in some instances provide both "coarse" and "fine" feedback to the novice user to help achieve a procedural outcome similar to that of a reference outcome (e.g., obtained from an expert user). Additional details of the architecture and operation of the MLM is provided in connection with subsequent figures.

Referring again to FIG. 1, software interfaces between the various components of the system 100 are included to allow the system components 200, 300, etc. to function together. A computer 700 is provided that includes the software interfaces as well as various other computer functionalities (e.g., computational elements, memory, processors, input/output elements, timers, etc.).

Figure 4:
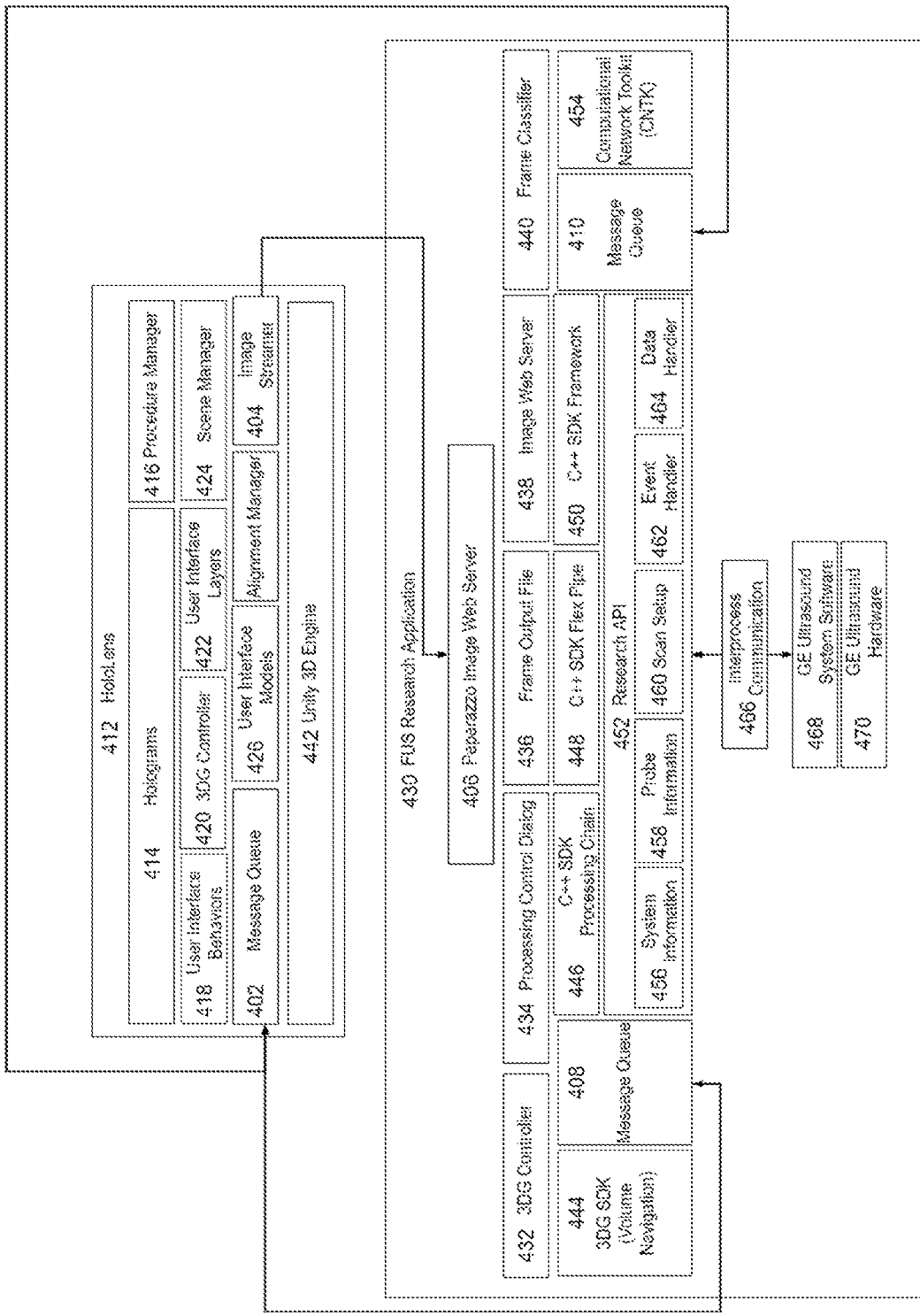
FIG. 4 is a diagram illustrating major software components in an experimental architecture for a system according to one embodiment of the present disclosure.

FIG. 4 illustrates the major software components in an experimental architecture for a system according to FIG. 1 for providing real-time 3D AR guidance in the use of a Flexible Ultrasound System (FUS) developed by NASA with a Microsoft HoloLens Head Mounted Display ARUI. In particular, FIG. 4 illustrates a software architecture for one embodiment of interfaces between computer 700 and 1) a medical equipment system 200 (i.e., the Flexible Ultrasound System), and 2) an ARUI 300 (i.e., the HoloLens Head Mounted Display ARUI). In some embodiments, these interfaces may be located within the medical equipment system or the ARUI, respectively, rather than in a separate computer.

Software components 402-410 are the software infrastructure modules used to integrate the FUS Research Application (FUSRA) 430 with the HoloLens Head Mounted Display (HMD) augmented reality (AR) application module 412. Although a wide range of architectures are possible, the integration for the experimental system of FIG. 4 uses a message queuing system for communication of status information, as well as command and state information (3D spatial data and image frame classification by deep machine learning) between the HoloLens ARUI and the FUS. Separately, the FUS ultrasound images are provided by a web server (discussed more fully below) dedicated to providing images for the HoloLens HMD AR application module 412 as an image stream.

The HoloLens HMD AR application module 412 software components are numbered 412-428. The main user interfaces provided by the HoloLens HMD AR application 412 are a Holograms module 414 and a Procedure Manager module 416. The Holograms module 414 blends ultrasound images, real world objects and 3D models, images and graphical clues for display in the HMD HoloLens ARUI. The Procedure Manager module 416 provides status and state for the electronic medical procedure being performed.

Figure 5:
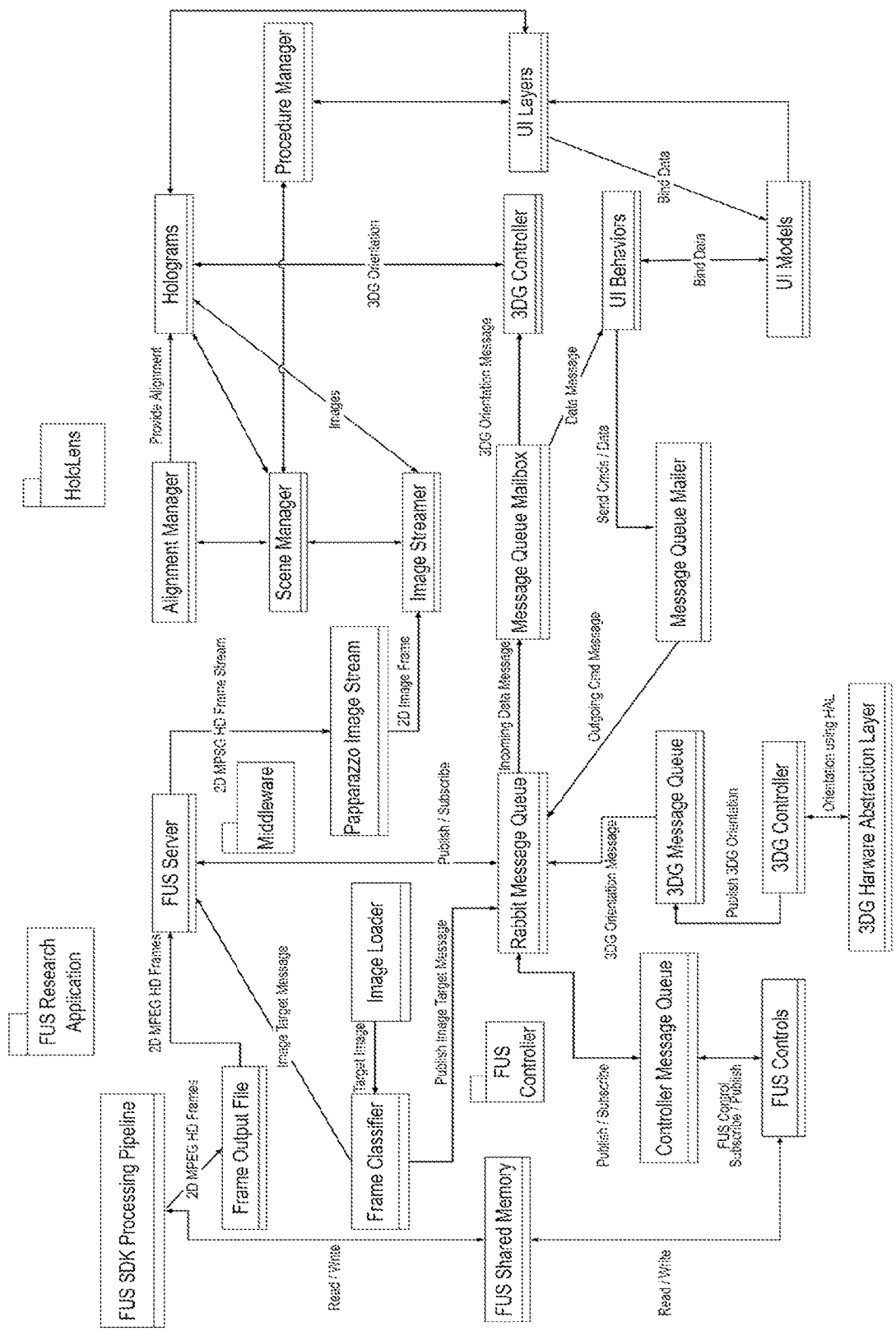
FIG. 5 is a software component diagram with more details of the software architecture of FIG. 4.

The FUS Research Application (FUSRA) module 430 components are numbered 430-440. The FUSRA module 430 will have capability to control the FUS ultrasound scan settings when messages (commands) are received by the computer from the FUS to change scan settings. Specific probe and specific scan settings are needed for specific ultrasound procedures. One specific example is the gain scan setting for the ultrasound, which is controlled by the Processing Control Dialog module 434 using the Message Queue 408 and C++ SDK Processing Chain 446 to control scan settings using C++ FUS shared memory (FIG. 5).

The FUSRA module 430 will have the capability to provide FUS ultrasound images in near-real time (high frame rate per second) so the HoloLens Head Mounted Display (HMD) Augmented Reality (AR) application module 412 can display the image stream. The FUSRA module 430 provides JPEG images as MJPEG through a web server 438 that has been optimized to display an image stream to clients (e.g., HoloLens HMD AR application module 412). The Frame Output File 436 (and SDL JPEG Image from FUS GPU, FIG. 5) provide images for the Paparazzo Image Web Server 406 and Image Web Server 438.

The FUSRA module 430 is also capable of providing motion tracking 3D coordinates and spatial awareness whenever the 3D Guidance System (3DGS) 400 (FIG. 1) is operating and providing data. The FUSRA module 430 uses the positional data received from the 3DGS 400 for motion tracking. The 3DGS 400 will provide spatial data (e.g., 3D position and rotation data) of tracked objects (e.g., the ultrasound probe) to clients using a Message Queue module 408. This is also referenced in FIG. 4 by 3DG Controller 420 and Message Queue module 402, which communicates with the 3DGS 400 of FIG. 1.

The FUS software development kit (SDK) in the FUSRA module 430 contains rudimentary image processing software to provide JPEG images to the FUSRA. The FUSRA module 430 contains additional image processing for monitoring and improving image quality, which is part of the C++ FUS SDK Framework 450 providing images to the Image Web Server 438 in FIG. 4.

The FUSRA module 430 uses the machine learning module (MLM) 600 (FIG. 1) for providing deep machine learning capabilities. The MLM 600 includes a neural network to be "trained" so that it "learns" how to interpret ultrasound images obtained by a novice user to compare to a "baseline" set of images from a reference performance of an ultrasound procedure (e.g., by an expert). The MLM 600 will generate image classification data to classify ultrasound images. The classification of images is the basis for the real-time outcome-based guidance provided to the novice user via the ARUI 300 (e.g., HoloLens Head Mounted Display device) during the performance of an ultrasound procedure. The image classification data will be provided to the HoloLens HMD AR application module 412 through a message queue 410 using the Computational Network toolkit (CNTK) 454 in FIG. 4.

The HoloLens HMD AR application module 412 provides a hands-free head mounted display ARUI platform for receiving and viewing real-time feedback during an ultrasound procedure. It also allows the novice user to focus on the patient without having to focus away from the patient for guidance.

The HoloLens HMD AR application module uses the HoloLens HMD platform from Microsoft and the Unity 3D game engine 442 from Unity. The HoloLens HMD AR application module 412 displays guidance during execution of the ultrasound medical procedure with AR visual clues and guidance, in addition to the ultrasound image that is also visible through the HoloLens HMD display. The HoloLens HMD AR application module 412 also has the capability to control the FUS scan settings as part of the procedure setup.

The architecture is designed to be extended to utilize electronic procedures or eProc. Once an electronic procedure is created (using an electronic procedure authoring tool) the procedure can be executed with the Procedure Manager module 416.

The HoloLens HMD AR application module 412 includes the capability to align 3D models and images in the holographic scene with real world objects like the ultrasound unit, its probe and the patient. This alignment allows virtual models and images to align with real world objects for rendering in the HoloLens head mounted display.

The HoloLens HMD AR application module 412 uses voice-based navigation by the novice user to maintain hands free operation of the ultrasound equipment, except during initialization when standard keyboard or other interfaces may be used for control. Voice command modules in FIG. 4 include the User Interface Behaviors module 418, User Interface Layers 422, and Scene Manager 424.

The HoloLens HMD AR application module 412 also is capable of controlling the FUS settings as part of the procedure setup. This function is controlled by the 3DG 400 (FIG. 1) using the Message Queue 402.

The HoloLens HMD AR application module 412 provides an Image Stream module 404 for display of ultrasound images that can be overlaid with guidance clues prompting the user to correctly the position the ultrasound probe. The HoloLens HMD AR application 412 is also capable of displaying 3D models and images in the HoloLens HMD along with real world objects like the ultrasound, its probe and the patient. The HoloLens HMD display allows virtual models and images to render over real world objects within the novice user's view. This is provided the Image Streamer 404 supplying images to the Holograms module 414 through the User Interface Layers module 422, User Interface Models module 426, and Scene Manager module 424. This image stream is the same kind of image as a regular display device but tailored for HMD.

FIG. 5 shows a software component diagram with more details of the software architecture of FIG. 4. Specifically, it shows the components allocated to the FUSRA module 430 and to the HoloLens HMD AR application module 412. Interactions among the software components are denoted by directional arrows and labels in the diagram. The FUSRA module 430 and the HoloLens HMD AR application module 412 use robust connectivity that is light weight and performs well. This is depicted in Figure by using edges components of FIG. 4, which include Message Queue modules 402, 408, and 410, as well as Image Streamer module 404 and Paparazzo Image Web Server module 406. The latter is dedicated to supplying the ultrasound image stream from the FUSRA module 430 to the HoloLens HMD AR application module 412. While the Paparazzo Image Web Server module 406 in some embodiments also sends other data to the HoloLens HMD AR application module 412, in one embodiment it is dedicated to images. Message Queues 402, 408, 410 are used for FUS scan setting controls and values, motion tracking, image classification, and other state data about the FUS. In addition, they provide much of the data required for the MLM 600 to generate and provide guidance to the HoloLens HMD AR application module 412. The architecture of FIGS. 4 and 5 is illustrative only and is not intended to be limiting.

Figure 2:
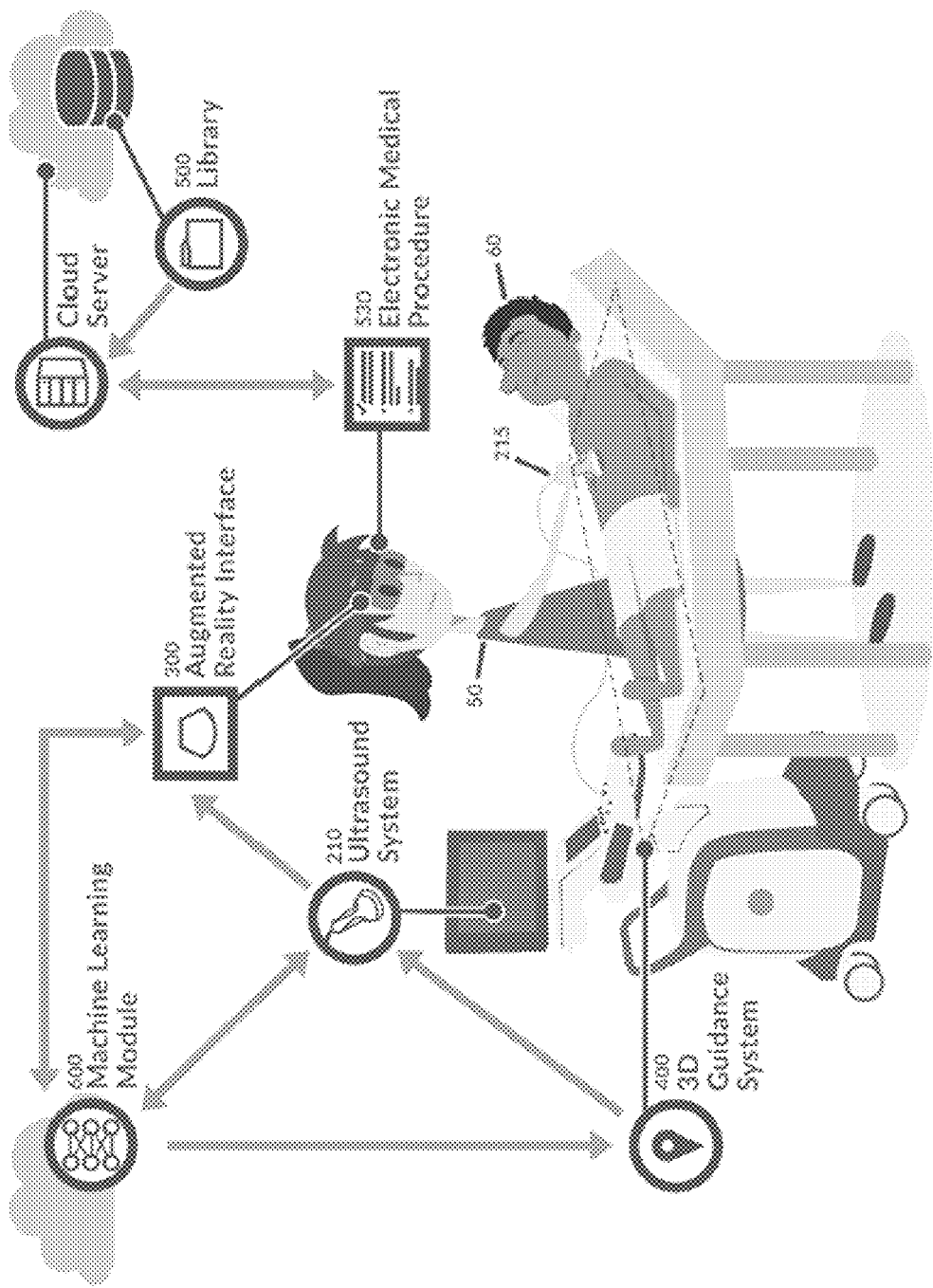
FIG. 2 is a diagram showing communication among the modules of a real-time, 3D AR feedback guidance system for the use of an ultrasound system, according to one embodiment.

An embodiment of a particular system for real-time, 3D AR feedback guidance for novice users of an ultrasound system, showing communication between the system modules, is provided in FIG. 2. An ultrasound system 210 is provided for use by a novice user 50 to perform an ultrasound medical procedure on a patient 60. The ultrasound system 210 may be any of a number of existing ultrasound systems, including the previously described Flexible Ultrasound System (FUS) for use in a space exploration environment. Other ultrasound systems, such as the GE Logiq E90 ultrasound system, and the Titan portable ultrasound system made by Sonosite, may be used, although it will be appreciated that different software interfaces may be required for different ultrasound systems.

The ultrasound system 210 may be used by novice user 50 to perform a variety of diagnostic procedures for detecting one or more medical conditions, which may include without limitation carotid assessments, deep vein thrombosis, cardiogenic shock, sudden cardiac arrest, and venous or arterial cannulation. In addition to the foregoing cardiovascular uses, the ultrasound system 210 may be used to perform procedures in many other body systems, including body systems that may undergo changes during zero gravity space operations. Procedures that may be performed include ocular examinations, musculoskeletal examinations, renal evaluation, and cardiac (i.e., heart) examinations.

In some embodiments, imaging data from the ultrasound system 210 is displayed on an augmented reality user interface (ARUI) 300. A wide variety of available ARUI units 300, many comprising a Head-Mounted Display (HMD), may be used in systems of the present invention. These may include the Microsoft HoloLens, the Vuzix Wrap 920AR and Star 1200, Sony HMZ-T1, Google Glass, Oculus Rift DK1 and DK2, Samsung GearVR, and many others. In some embodiments, the system can support multiple ARUIs 300, enabling multiple or simultaneous users for some procedures or tasks, and in other embodiments allowing third parties to view the actions of the user in real time (e.g., suitable for allowing an expert user to train multiple novice users).

Information on a variety of procedures that may be performed by novice user 50 may be provided by Library 500, which in some embodiments may be stored on a cloud-based server as shown in FIG. 2. In other embodiments, the information may be stored in a conventional memory storage unit. In one embodiment, the library 500 may obtain and display via the ARUI 300 an electronic medical procedure 530, which may include displaying step-by-step written, visual, audio, and/or tactile instructions for performing the procedure.

As shown in FIG. 2, a 3D guidance system (3DGS) 400 may map the space for the medical procedure and may track the movement of a portion of the medical device system 100 by a novice user (50) as he or she performs a medical procedure. In one nonlimiting example, the 3DGS 400 track the movement of the probe 215 of the ultrasound system 210, which is used to obtain images.

In some embodiments, the 3DGS 400, either alone or in combination with library 500 and/or machine learning module (MLM) 600, may cause ARUI 300 to display static markers or arrows to complement the instructions provided by the electronic medical procedure 530. The 3DGS 400 can communicate data relating to the movements of probe 215, while a user is performing a medical procedure, to the MLM 600.

The machine learning module (MLM) 600 compares the performance of the novice user 50 to that of a reference performance (e.g., by an expert user) of the same procedure as the novice user. As discussed regarding FIG. 1, MLM 600 may provide real-time feedback to the novice user via the ARUI 300. The real-time feedback may include either or both of position-based feedback using data from the 3DGS 400, as well as outcome-based feedback from the ultrasound system 210.

The MLM 600 generates position-based feedback by comparing the actual movements of a novice user 50 (e.g., using positioning data received from the 3DGS 400 tracking the movement of the ultrasound probe 215) to reference data for the same task. In one embodiment, the reference data is data obtained by an expert performing the same task as the novice user. The reference data may be either stored in MLM 600 or retrieved from library 500 via a computer (not shown). Data for a particular patient's anatomy may also be stored in library 500 and used by the MLM 600.

Based on the comparison of the novice user's movements to those of the expert user, the MLM 600 may determine in real time whether the novice user 50 is acceptably performing the task or procedure (i.e., within a desired margin of error to that of an expert user). The MLM 600 may communicate with ARUI 300 to display real time position-based feedback guidance in the form of data and/or instructions to confirm or correct the user's performance of the task based on the novice user movement data from the 3DGS 400 and the reference data. By generating feedback in real-time as the novice user performs the medical procedure, MLM 600 thereby enabling the novice user to correct errors or repeat movements as necessary to achieve an outcome for the medical procedure that is within a desired margin to that of reference performance.

In addition to the position-based feedback generated from position data received from 3DGS 400, MLM 600 in the embodiment of FIG. 2 also provides outcome-based feedback based on comparing the ultrasound images generated in real-time by the novice user 50 to reference images for the same medical procedure stored in the library 500. Library 500 may include data for multiple procedures and/or tasks to be performed using a medical device system such as ultrasound system 210. In alternative embodiments, only one type of real-time feedback (i.e., position-based feedback or outcome-based feedback) is provided to guide a novice user. The type of feedback (i.e., based on position or the outcome of the medical procedure) may be selected based on the needs of the particular learning environment. In some types of equipment, for example, feedback generated by MLM solely based on the novice user's manipulation of a portion of the equipment (i.e., movements of a probe, joystick, lever, rod, etc.) may be adequate to correct the novice user's errors, while in other systems information generated based on the outcome achieved by the user (outcome-based feedback) may be adequate to correct the novice user's movements without position-based feedback.

Although FIG. 2 is directed to an ultrasound system, it will be appreciated that in systems involving different types of medical (e.g., a cardiogram), or non-medical equipment, the outcome-based feedback may be based not on the comparison of images but on numerical, graphical, or other forms of data. Regardless of the type of equipment used, outcome-based feedback is generated by the MLM 600 based on data generated by the equipment that indicates whether or not the novice user successfully performed a desired task or procedure. It will be further appreciated that in some embodiments of the present invention, outcome-based feedback may be generated using a neural network, while in other embodiments, a neural network may be unnecessary.

In one embodiment, one or both of real-time motion-based feedback and outcome-based feedback may be used to generate a visual simulation (e.g., as a narrated or unnarrated video displayed virtually to the novice user in the ARUI 300 (e.g., a HoloLens headset). In this way, the novice user may quickly (i.e., within seconds of performing a medical procedure) receive feedback indicating deficiencies in technique or results, enabling the user to improve quickly and achieve outcomes similar to those of a reference performance (e.g., an expert performance) of the medical or other equipment.

In one embodiment, the novice user's performance may be tracked over time to determine areas in which the novice user repeatedly fails to implement previously provided feedback. In such cases, training exercises may be generated for the novice user focusing on the specific motions or portions of the medical procedure that the novice user has failed to correct, to assist the novice user to achieve improved results. For example, if the novice user fails to properly adjust the angle of an ultrasound proper at a specific point in a medical procedure, the MLM 600 and/or computer 700 may generate a video for display to the user that this limited to the portion of the procedure that the user is performing incorrectly. This allows less time to be wasted having the user repeat portions of the procedure that the user is correctly performing, and enables the user to train specifically on areas of incorrect technique.

In another embodiment, the outcome-based feedback may be used to detect product malfunctions. For example, if the images being generated by a novice user at one or more points during a procedure fail to correspond to those of a reference (e.g., an expert), or in some embodiments by the novice user during prior procedures, the absence of any other basis for the incorrect outcome may indicate that the ultrasound machine is malfunctioning in some way.

In one embodiment, the MLM 600 may provide further or additional instructions to the user in real-time by comparing the user's response to a previous real-time feedback guidance instruction to refine or further correct the novice user's performance of the procedure. By providing repeated guidance instruction as the novice user refines his/her technique, MLM 600 may further augment previously-provided instructions as the user repeats a medical procedure or portion thereof and improves in performance. Where successful results for the use of a medical device are highly technique sensitive, the ability to "fine tune" the user's response to prior instructions may help maintain the user on the path to a successful outcome. For example, where a user "overcorrects" in response to a prior instruction, the MLM 600, in conjunction with the 3DGS 400, assists the user to further refine the movement to achieve a successful result.

To provide usable real time 3D AR feedback-based guidance to a medical device user, the MLM 600 may include a standardized nomenclature module (not shown) to provide consistent real-time feedback instructions to the user. In an alternative embodiment, multiple nomenclature options may be provided to users, and different users may receive instructions that vary based on the level of skill and background of the user. For example, users with an engineering background may elect to receive real time feedback guidance from the machine learning module 600 and ARUI 300 in terminology more familiar to engineers, even where the user is performing a medical task. Users with a scientific background may elect to receive real time feedback guidance in terminology more familiar for their specific backgrounds. In some embodiments, or for some types of equipment, however, a single, standardized nomenclature module may be provided, and the machine learning module 600 may provide real time feedback guidance using a single, consistent terminology.

The MLM 600 may also provide landmarks and virtual markings that are informative to enable the user to complete the task, and the landmarks provided in some embodiments may be standardized for all users, while in other embodiments different markers may be used depending upon the background of the user.

Figure 3:
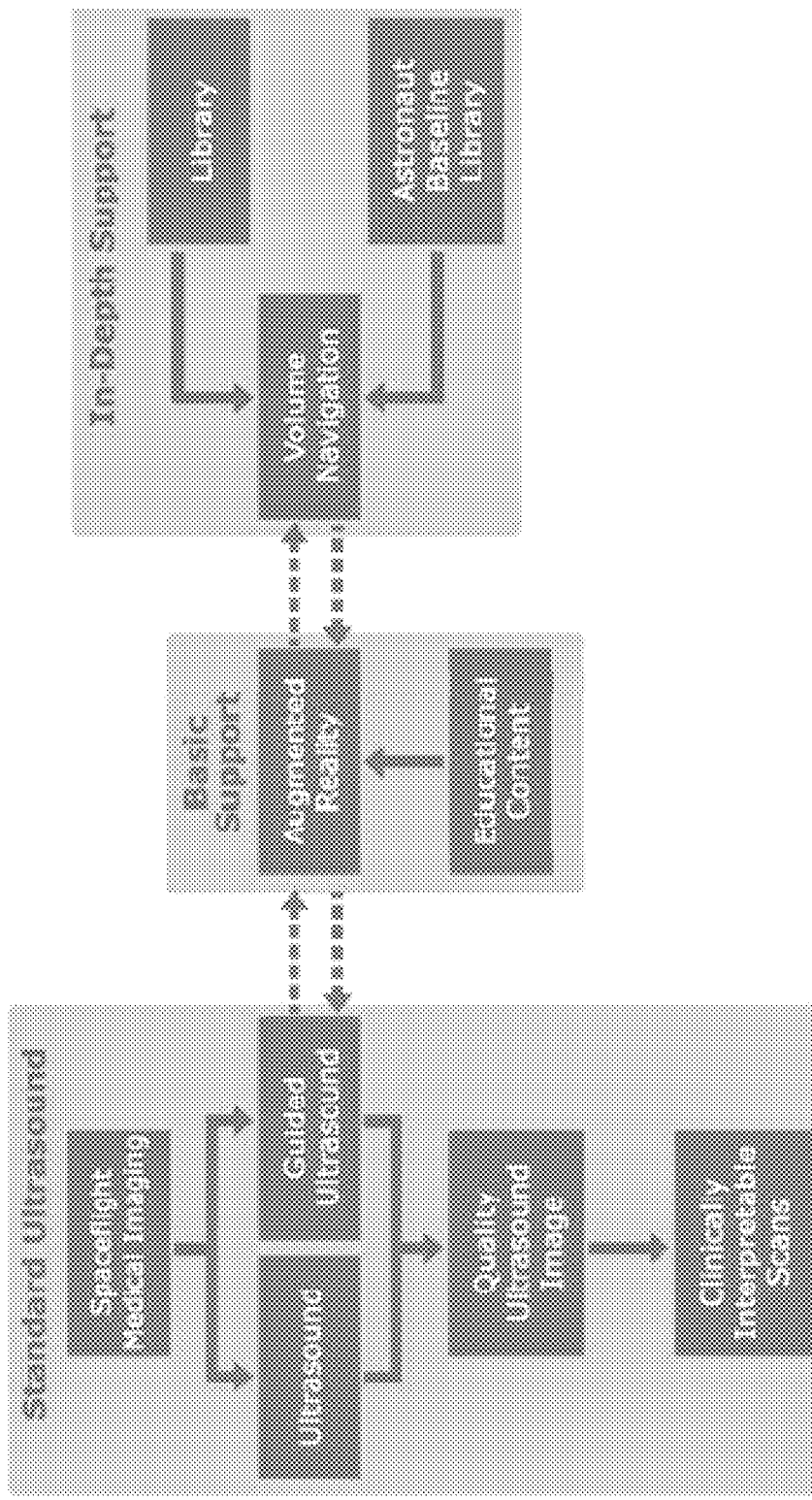
FIG. 3 is a diagram showing an ultrasound system that may include multiple modes of operation, involving different levels of Augmented Reality functions.

FIG. 3 illustrates a continuum of functionality of an ultrasound system that may include both standard ultrasound functionality in a first mode, in which no AR functions are used, as well as additional modes involving AR functions. A second, "basic support" mode may also be provided with a relatively low level of Augmented Reality supplementation, e.g., an electronic medical procedure display and fixed markers. A third mode, incorporating real-time, three-dimensional (3D) augmented reality (AR) feedback guidance, may also be selected.

In the embodiment of FIG. 2, MLM 600 provides outcome-based feedback by comparing novice user ultrasound images and reference ultrasound images using a neural network. The description provided herein of the use of such neural networks is not intended to limit embodiments of the prevent invention to the use of neural networks, and other techniques may be used to provide outcome-based feedback.

A variety of neural networks may be used in MLM 600 to provide outcome-based-feedback in a medical device system according to FIG. 1. Convolutional neural networks are often used in computer vision or image analysis applications. In systems involving image processing, such as FIG. 2, neural networks used in MLM 600 preferably include at least one convolutional layer, because image processing is the primary basis for outcome-based feedback. In one embodiment, the neural network may be ResNet, a neural network architecture developed by Microsoft Research for image classification. ResNet may be implemented in software using a variety of computer languages such as NDL, Python, or BrainScript. In addition to ResNet, other neural network architectures suitable for image classification may also be used in different embodiments. For different medical equipment systems, or non-medical equipment, it will be appreciated that other neural networks, having features more applicable to a different type of data generated by that equipment, may be preferred.

In one embodiment of FIG. 2, ResNet may be used in the MLM 600 to classify a continuous series of ultrasound images (e.g., at a desired sampling rate such as 20 frames per second) generated by the novice user 50 in real-time using ultrasound system 210. The images are classified into groups based on whether the desired outcome is achieved, i.e., whether the novice user's images match corresponding reference images within a desired confidence level. The goal of classification is to enable the MLM to determine if the novice user's images capture the expected view (i.e., similar to the reference images) of target anatomical structures for a specified ultrasound medical procedure. In one embodiment, the outcome-based feedback provided by the MLM 600 includes 1) the most-probable identity of the ultrasound image (e.g., the name of a desired structure such as "radial cross-section of the carotid artery," "lateral cross-section of the jugular vein," etc.), and 2) the probability of identification (e.g., 0% to 100%).

As an initial matter, ultrasound images from ultrasound system 210 must be converted to a standard format usable by the neural network (e.g., ResNet). For example, ultrasound images captured by one type of ultrasound machine (FUS) are in the RGB24 image format, and may generate images ranging from 512×512 pixels to 1024×768 pixels, depending on how the ultrasound machine is configured for an ultrasound scan. During any particular scan, the size of all captured images will remain constant, but image sizes may vary for different types of scans. Neural networks, however, generally require that the images must be in a standardized format (e.g., CHW format used by ResNet) and a single, constant size determined by the ML model. Thus, ultrasound images may need to be converted into the standardized format. For example, images may be converted for use in ResNet by extracting the CHW components from the original RGB24 format to produce a bitmap in the CHW layout, as detailed at https://docs.microsoft.com/en-us/cognitive-toolkit/archive/cntk-evaluate-image-transforms. It will be appreciated that different format conversion processes may be performed by persons of skill in the art to produce images usable by a particular neural network in a particular implementation.

Ultrasound medical procedures require the ultrasound user to capture specific views of various desired anatomical structures from specific perspectives. These view/perspective combinations may be represented as classes in a neural network. For example, in a carotid artery assessment procedure, the ultrasound user may be required to first capture the radial cross section of the carotid artery, and then capture the lateral cross section of the carotid artery. These two different views can be represented as two classes in the neural network. To add additional depth, a third class can be used to represent any view that does not belong to those two classes.

Classification is a common machine learning problem, and a variety of approaches have been developed. Applicants have discovered that a number of specific steps are advisable to enable MLM 600 to have good performance in classifying ultrasound images to generate 3D AR feedback guidance that is useful for guiding novice users. These include care in selecting both the training set and the validation data set for the neural network, and specific techniques for optimizing the neural network's learning parameters.

As noted, ResNet is an example of a neural network that may be used in MLM 600 to classify ultrasound images. Additional information on ResNet may be found at https://arxiv.org/abs/1512.03385. Neural networks such as ResNet are typically implemented in a program language such as NDL, Python, or BrainScript, and then trained using a deep machine learning (DML) platform or program such as CNTK, Caffe, or Tensorflow, among other alternatives. The platform operates by performing a "training process" using a "training set" of image data, followed by a "validation process" using a "validation set" of image data. Image analysis in general (e.g., whether part of the training and validation processes, or to analyze images of a novice user) is referred to as "evaluation" or "inferencing."

In the training process, the DML platform generates a machine learning (ML) model using the training set of image data. The ML model generated in the training process is then evaluated in the validation process by using it to classify images from the validation set of image data that were not part of the training set. Regardless of which DML platform (e.g., CNTK, Caffe, Tensorflow, or other system) is used, the training and validation performance of ResNet should be be similar for a given type of equipment (medical or non-medical). In particular, for the Flexible Ultrasound System (FUS) previously described, the image analysis performance of ResNet is largely independent of the DML platform.

In one embodiment, for small patient populations (e.g., astronauts, polar explorers, small maritime vessels), for each ultrasound procedure, a patient-specific machine learning model may be generated during training using a training data set of images that are acquired during a reference examination (e.g., by an expert) for each individual patient. Accordingly, during subsequent use by a novice user, for each particular ultrasound procedure the images of a specific patient will be classified using a patient-specific machine learning module for that specific patient. In other embodiments, a single "master" machine learning model is used to classify all patient ultrasound images. In patient-specific approaches, less data is required to train the neural network to accurately classify patient-specific ultrasound images, and it is easier to maintain and evolve such patient-specific machine learning models.

Regardless of which DML platform is used, the machine learning (ML) model developed by the platform has several common features. First, the ML model specifies classes of images that input images (i.e., by a novice user) will be classified against. Second, the ML model specifies the input dimensions that determines the required size of input images. Third, the ML model specifies the weights and biases that determine the accuracy of how input images will the classified.

The ML model developed by the DLM platform is the structure of the actual neural network that will be used in evaluating images captured by a novice user 50. The optimized weights and biases of the ML model are iteratively computed and adjusted during the training process. In the training process, the weights and biases of the neural network are determined through iterative processes known as Feed-Forward (FF) and Back-Propagation (BP) that involve the input of training data into an input layer of the neural network and comparing the corresponding output at the network's output layer with the input data labels until the accuracy of the neural network in classifying images is at an acceptable threshold accuracy level.

The quality of the training and validation data sets determines the accuracy of the ML model, which in turn determines the accuracy of the neural network (e.g., ResNet) during image classification by a novice user. A high-quality data set is one that enables the neural network to be trained within a reasonable time frame to accurately classify a massive variety of new images (i.e., those that do not appear in the training or validation data sets). Measures of accuracy and error for neural networks are usually expressed as classification error (additional details available at https://www.gepsoft.com/gepsoft/APS3 KB/Chapter09/Section2/SS01.htm), cross entropy error (https://en.wikipedia.org/wiki/Cross_entropy), and mean average precision (https://docs.microsoft.com/en-us/cognitive-toolkit/object-detection-using-fast-r-cnn-brainscript#map-mean-average-precision).

In one embodiment, the output of the neural network is the probability, for each image class, that an image belongs to the class. From this output, the MLM 600 may provide outcome-based feedback to the novice user of one or both of 1) the best predicted class for the image (i.e., the image class that the neural network determines has the highest probability that the image belongs to the class), and 2) the numerical probability (e.g., 0% to 100%) of the input image belonging to the best predicted class. The best predicted class may be provided to the novice user in a variety of ways, e.g., as a virtual text label, while the numerical probability may also be displayed in various ways, e.g., as a number, a number on a color bar scale, as a grayscale color varying between white and black, etc.

To train a neural network such as ResNet to classify ultrasound images for specific ultrasound procedures performed with ultrasound system 210, many high quality images are required. In many prior art neural network approaches to image classification, these data sets are manually developed in a highly labor-intensive process. In one aspect, the present disclosure provides systems and methods for automating one or more portions of the generation of training and validation data sets.

Using software to automate the process of preparing accurately labeled image data sets not only produces data sets having minimal or no duplicate images, but also enables the neural network to be continuously trained to accurately classify large varieties of new images. In particular, automation using software allows the continual generation or evolution of existing image data sets, thereby allowing the continual training of ResNet as the size of the image data set grows over time. In general, the more high-quality data there is to train a neural network, the higher the accuracy of the neural network's ability to classify images will be. This approach contrasts sharply with the manual approaches to building and preparing image data sets for deep machine learning.

As one nonlimiting example, an ultrasound carotid artery assessment procedure requires at least 10,000 images per patient for training a patient-specific neural network used to provide outcome-based feedback to a novice user in a 3D AR medical guidance system of the present disclosure. Different numbers of images may be used for different imaging procedures, with the number of images will depending upon the needs of the particular procedure.

The overall data set is usually split into two subsets, with 70-90%, more preferably 80-85%, of the images being included as part of a training set and 10-30%, more preferably 15-20%, of the images included in the validation data set, with each image being used in only one of the two subsets (i.e., for any image in the training set, no duplicate of it should exist in the validation set. In addition, any excessive number of redundant images in the training set should be removed to prevent the neural network from being overfitted to a majority of identical images. Removal of such redundant images will improve the ability of the neural network to accurately classify images in the validation set. In one embodiment, an image evaluation module evaluates each image in the training set to determine if it is a duplicate or near-duplicate of any other image in the database. The image evaluation module computes each image's structural similarity index (SSI) against all other images in the set. If the SSI between two images is greater than a similarity threshold, which in one nonlimiting example may be about 60%, then the two images are regarded as near duplicates and the image evaluation module removes all one of the duplicate or near duplicate images. Further, images that are down to exist both in the training set and the validation set are likewise removed (i.e., the image evaluation module computes SSI values for each image in the training set against each image in the validation set, and removes duplicate or near-duplicate images from one of the training and validation sets). The reduction of duplicate images allows the neural network to more accurately classify images in the validation set, since the chance of overfitting the neural network during training to a majority of identical images is reduced or eliminated.

Figure 6:
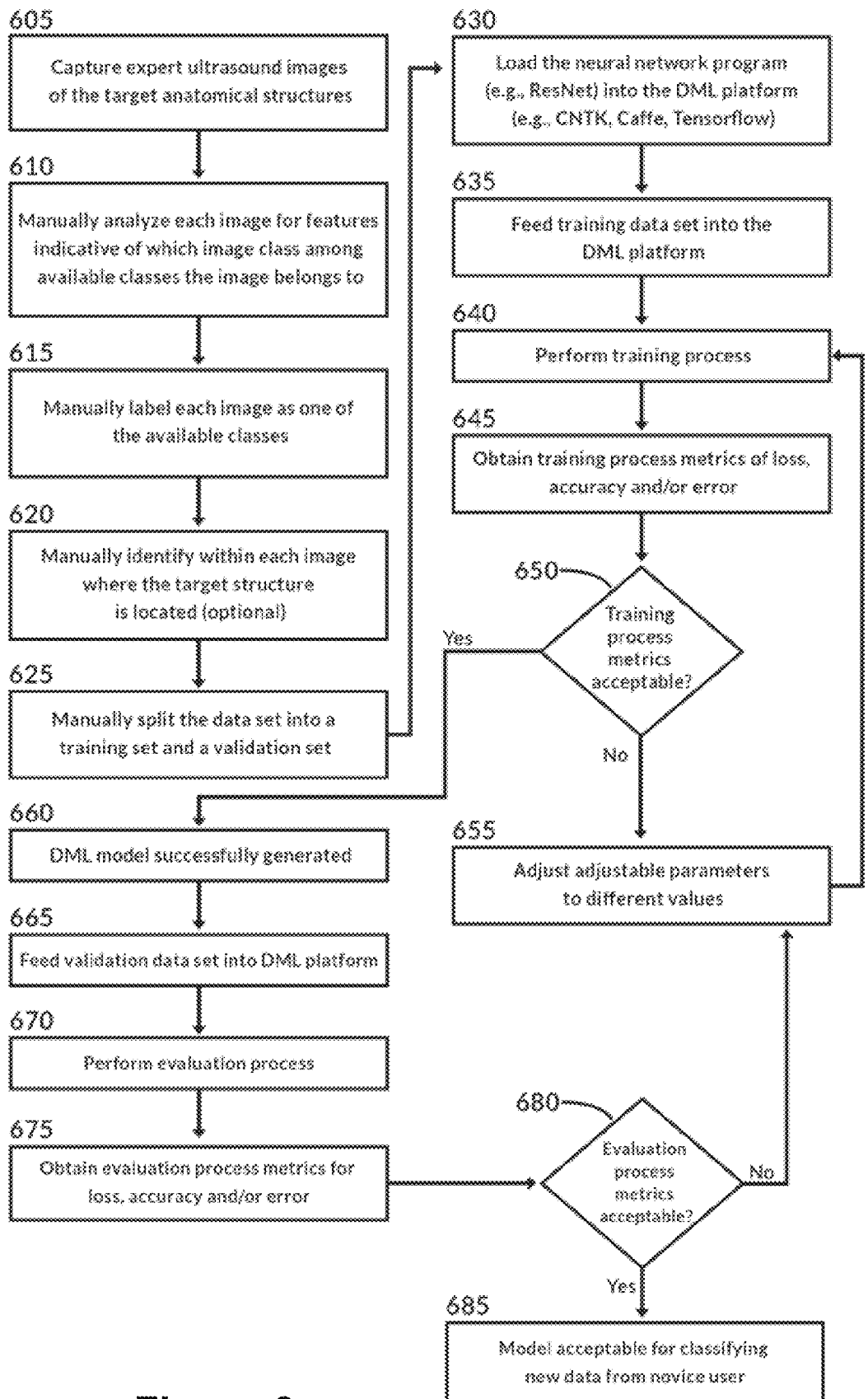
FIG. 6 is a flowchart of a method for developing a machine learning module using manually prepared data sets.

FIG. 6 illustrates a method 602 for developing a ML model for training a neural network using manually prepared data sets. First, a reference user (e.g., an expert sonographer or ultrasound technician) captures (610) all the necessary ultrasound views of the target anatomical structures for the ultrasound carotid artery assessment (or medical procedure), including 10,000 or more images. The population size of each view or class should be equal. For the carotid artery assessment, the radial, lateral, and unknown views are captured, which is around 3,300+ images per view or class.

Next the reference user manually labels (615) each image as one of the available classes. For the carotid artery assessment, the images are labeled as radial, lateral or unknown.no image overlap in the training and validation data sets). For each labeled image, the reference user may in some embodiments (optional), manually identify (620) the exact area within the image where the target anatomical structure is located, typically with a box bounding the image. Two examples of this the use of bounding boxes to isolate particular structures are provided in FIGS. 10A and 10B, which shows the location of a carotid artery within an ultrasound image.

Once the entire data set is properly labeled, it is manually split (625) into the training data set and the validation data sets, which may then be used to train the neural network (e.g., ResNet). Neural networks comprise a series of coupled nodes organized into at least an input and an output layer. Many neural networks have one or more additional layers (commonly referred to as "hidden layers") that may include one or more convolutional layers as previously discussed regarding MLM 600.

The method 600 also comprises loading (630) the neural network definition (such as a definition of ResNet), usually expressed as a program in a domain-specific computer language such as NDL, Python or BrainScript, into a DML platform or program such as CNTK, Caffe or Tensorflow. The DML platforms offer tunable or adjustable parameters that are used to control the outcome of the training process. Some of the parameters are common to all DML platforms, such as types of loss or error, accuracy metrics, types of optimization or back-propagation (e.g., Stochastic Gradient Descent and Particle Swarm Optimization). Some adjustable parameters are specific to one or more of the foregoing, such as parameters specific to Stochastic Gradient Descent such as the number of epochs to train, training size (e.g., mini-batch), learning rate constraints, and others known to persons of skill in the art. In one example involving CNTK as the DML platform, the adjustable parameters include learning rate constraints, number of epochs to train, epoch size, minibatch size, and momentum constraints.

The neural network definition (i.e., a BrainScript program of ResNet) itself also has parameters that may be adjusted independently of any parameter adjustments or optimization of parameters in the DML platform. These parameters are defined in the neural network definition such as the connections between deep layers, the types of layers (e.g., convolutional, max pooling, ReLU), and their structure/organization (e.g., dimensions and strides). If there is minimal error or high accuracy during training and/or validating, then adjustment of these parameters may have a lesser effect on the overall image analysis performance compared to adjusting parameters not specific to the neural network definition (e.g., DML platform parameters), or simply having a high quality training data set. In the case of a system developed for carotid artery assessment, no adjustments to the neural network parameters were needed to achieve less than 10%-15% error, in the presence of a high quality training data set.

Referring again to FIG. 6, the methods also includes (635) feeding the training data set into the DML platform and performing the training process (640). After the training process is completed, training process metrics for loss, accuracy and/or error are obtained (645). A determination is made (650) whether the training process metrics are within an acceptable threshold for each metric. If the training process metrics are outside of an acceptable threshold for the relevant metrics, the adjustable parameters are adjusted to different values (655) and the training process is restarted (640). Parameter adjustments may be made one or more times. However, if the training process 640 fails to yield acceptable metrics (650) after a threshold number of iterations or repetitions (e.g., two, three or another number), then the data set is insufficient to properly train the neural network and it is necessary to regenerate the data set. If the metrics are within an acceptable threshold for each metric, then a ML model has been successfully generated (660). In one embodiment, acceptable thresholds may range from less than 5% to less than 10% average cross-entropy error for all epochs, and from less than 15% to less than 10% average classification error for all epochs. If will be recognized that different development projects may involve different acceptable thresholds.

The method then includes feeding the validation data set to the ML model (665), and the validation process is performed (670) using the validation data set. After the completion of the validation process, validation process metrics for loss, accuracy and/or error are obtained (675) for the validation process. A determination is made (680) whether the validation metrics are within an acceptable threshold for each metric, which may be the same as or different from those used for the training process. If the validation process metrics are outside of the acceptable thresholds, the adjustable parameters are adjusted to different values (655) and the training process is restarted (640). If the metrics are acceptable, then the ML model may be used to classify new data (685).

The process may be allowed to continue through one or more additional cycles. If validation process metrics are still unacceptable, then the data set is insufficient to properly train the neural network, and the data set needs to be regenerated.

Referring again to FIG. 6, the initial portions of the process are highly labor-intensive. Specifically, the steps of capturing ultrasound images (610), manually labeling (615) and identifying target areas are usually performed at great cost in time and expense by a reference user (e.g., a sonographer or ultrasound technician, nurse, or physician). In addition, splitting the data set into training and validation sets may also involve significant manual discretion by the reference user.

In one aspect, the present invention involves using computer software to automate or significantly speed up one or more of the foregoing steps. Although capturing ultrasound images during use of the ultrasound system by a reference or expert user (610) necessarily requires the involvement of an expert, in one embodiment the present disclosure includes systems and methods for automating all or portions of steps 610-625 of FIG. 6.

Figure 7:
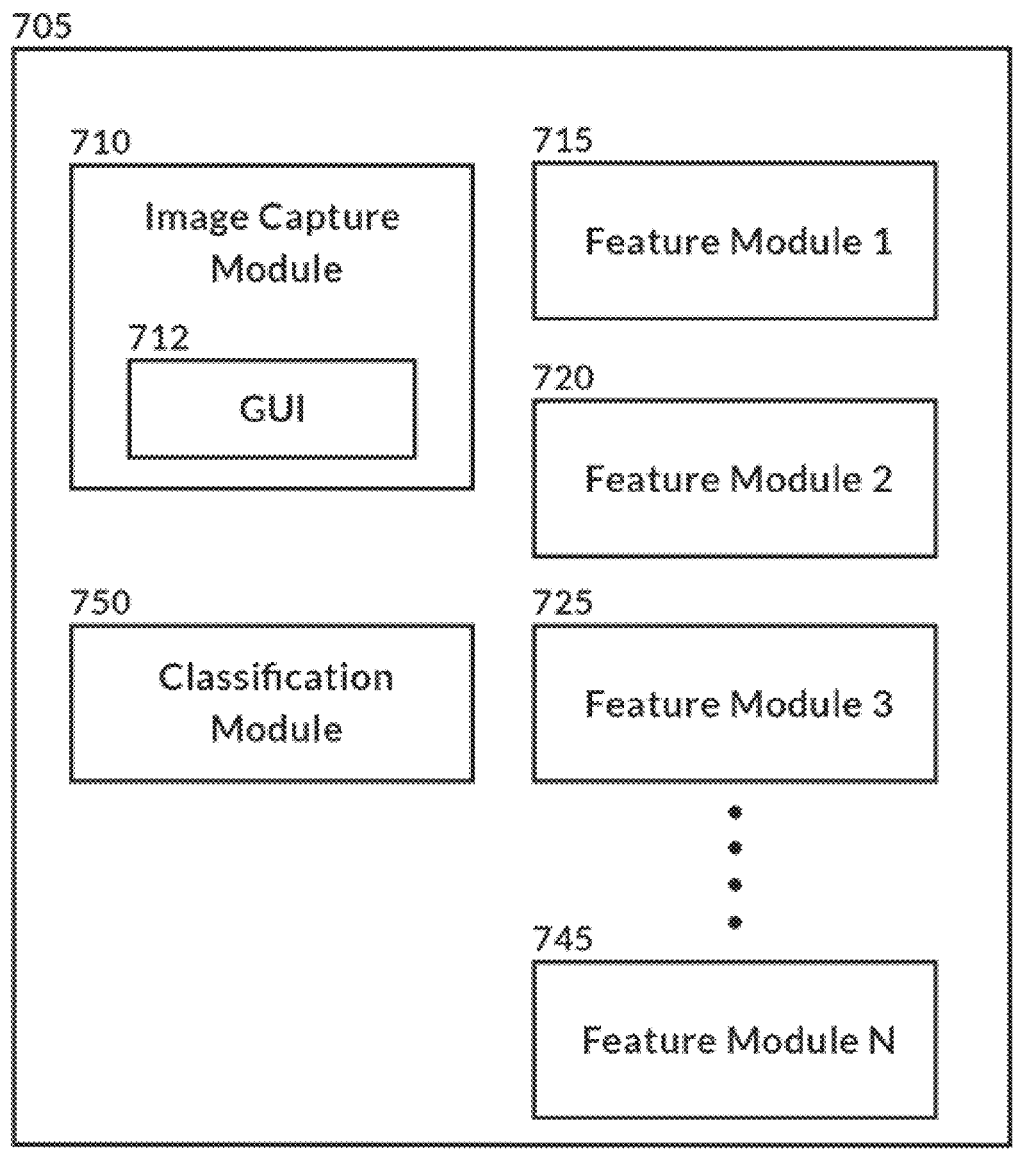
FIG. 7 is a block diagram of a machine learning development module.

FIG. 7 illustrates a machine learning development module (MLDM) 705 for automating some or all of the steps of developing training and validation image data sets for a particular medical imaging procedure, in this instance a carotid artery assessment procedure. I will be understood that multiple MLDMs, different from that shown in FIG. 7, may be provided for each imaging procedure for which 3D AR feedback is to be provided by a system according to FIG. 1. Manually capturing, labeling, isolating, and dividing the images into a two image data sets is not only time consuming and expensive, but is also error prone because of the subjective judgment that must be exercised by the reference user in labeling and isolating the relevant portions of each image captured for a given procedure. The accuracy and speed of these processes may be improved using automated image processing techniques to provide consistent analysis of the image patterns of target anatomical structures specific to a particular ultrasound medical procedure.

In one embodiment, MLDM 705 is incorporated into computer system 700 (FIG. 1) and communicates with an imaging medical equipment system (e.g., an ultrasound system 210, FIG. 2). Referring again to FIG. 7, MLDM 705 includes an image capture module 710 that may automatically capture images from the ultrasound system 210 while a reference user performs a carotid artery assessment associated with MLDM 705 (or a different procedure associated with a different MLDM). The image capture module 710 comprises one or more of hardware, firmware, software or a combination thereof, in computer 700 (FIG. 1).

Image capture module 710 may also comprise an interface such as a graphical user interface (GUI) 712 for display on a screen of computer 700 or ultrasound system 210. The GUI 712 may permit an operator (e.g., the reference user or a system developer) to automatically capture images while the reference user performs the medical procedure specific to MLDM 705 (e.g., a carotid artery assessment). More specifically, the GUI 712 enables a user to program the image capture module 710 to capture images automatically (e.g., at a specified time interval such as 10 Hz, or when 3DGS 400 detects that probe 210 is at a particular anatomical position) or on command (e.g., by a capture signal activated by the operator using a sequence of keystrokes on computer 700 or a button on ultrasound probe 215). The GUI 712 allows the user to define the condition(s) under which images are captured by image capture module 710 while the reference user performs the procedure of MLDM 705.

Once images have been captured (e.g., automatically or on command) by image capture module 710, MLDM 705 includes one or more feature modules (715, 720, 725, 745, etc.) to identify features associated with the various classes of images that are available for the procedure of MLDM 705. The features may be aspects of particular structures that define which class a given image should belong to. Each feature module defines the image criteria to determine whether a feature is present in the image. Depending on the number of features and the number of classes (which may each contain multiple features, MLDMs for different imaging procedures may have widely different numbers of feature modules. Referring again to FIG. 7, MLDM 705 applies each of the feature modules for the procedure to each image captured for that procedure to determine if and where the features are present in each captured image. An example of various features and how they may be defined in the feature modules is provided in FIGS. 9A-9G, discussed more fully below.

For example, in a carotid artery assessment procedure, the available classes may include a class of "radial cross section of the carotid artery," a class of "lateral cross section of the carotid artery," and a class of "unknown" (or "neither radial cross section nor lateral cross section"). For an image to be classified as belonging to the "radial cross section of the carotid artery" class, various features associated with the presence of the radial cross section of a carotid artery must be present in the image. The feature modules, e.g., 715, 720, etc., are used by the MLDM 705 to analyze captured images to determine whether a given image should be placed in the class of "radial cross section of the carotid artery" or in another class. Because the feature modules are each objectively defined, the analysis is less likely to be mislabeled because of the reference user's subjective bias.

Finally, each MLDM 705 may include a classification module 750 to classify each of the captured images with a class among those available for MLDM 705. Classification module 750 determines the class for each image based on which features are present and not present in the image, and labels each image as belonging to the determined class. Because the feature modules are each objectively defined, the classification module 750 is less likely to mislabel images than manual labeling based on the subjective judgment exercised by the reference user.

Computer 700 (FIG. 1) may include a plurality of MLDMs similar to module 705, each of which enables automating the process of capturing and labeling images for a different imaging procedure. It will be appreciated that different modules may be provided for automating the capture and labeling of data from different types of medical or non-medical equipment during their use by a reference user or expert. In one alternative embodiment, a central library (e.g., library 500, FIG. 1) of features may be maintained for all procedures for which 3D AR guidance to a novice user are to be provided by a system 100 of FIG. 1. In such an embodiment, the features (whether software, firmware, or hardware) are maintained separately from computer 700, and the structure of MLDMs such as MLDM 705 may be simplified such that each MLDM simply accesses or calls the feature modules for its particular procedure from the central feature library.

The automated capture and labeling of reference data by MLDM 705 may be better understood by an example of a carotid artery assessment using an ultrasound system. The radial and lateral cross-sections of the carotid artery have distinct visual features that can be used to identify their presence it ultrasound images at specific ultrasound depths. These visual features or criteria may be defined and stored as feature modules 715, 720, 725, etc. in MLDM 705 (or a central feature library in alternative embodiments) for a carotid artery assessment procedure. Captured images are then analyzed using the feature modules determine whether or not each of the carotid artery assessment features are present. The presence or absence of the features are then used to classify each image into one of the available classes for the carotid artery assessment procedure.

The feature modules 715, 720, 725, etc. provide consistent analysis of image patterns of the target anatomical structures in the images captured during a reference carotid artery assessment procedure (e.g., by an expert). Feature modules for each image class may be defined by a reference user, a system developer, or jointly by both, for any number of ultrasound procedures such as the carotid artery assessment procedure.

Once the features for each carotid artery assessment procedure image class have been defined and stored as feature modules 715, 720, 725, etc., standard image processing algorithms (e.g., color analysis algorithms, thresholding algorithms, convolution with kernels, contour detection and segmentation, clustering, and distance measurements) are used in conjunction with the defined features to identify and measure whether the features are present in the captured reference images. In this way, the feature modules allow the MLDM 705 to automate (fully or partially) the labeling of large data sets in a consistent and quantifiable manner.

The visual feature image processing algorithms, in one embodiment, are performed on all of the images that are captured during the reference performance of the particular medical procedure associated with the feature module, using software, firmware and/or hardware. The ability of the labeling module to label images may be verified by review of the automated labeling of candidate images by a reference user (e.g., an expert sonographer, technician, or physician). The foregoing processes and modules allow developers and technicians to quickly and accurately label and isolate target structures in large image data sets of 10,000 or more images.

MLDMs as shown in FIG. 7 facilitate consistent labeling because the visual features are determined numerically by standard algorithms after being defined by a reference user, expert, or system developer. The automated labeling is also quantified, because the features are determined numerically according to precise definitions.

Although the functions and operation of MLDM 705 have been illustrated for a carotid artery assessment ultrasound procedure, it will be appreciated that additional modules (not shown) may be provided for different ultrasound procedures (e.g., a cardiac assessment procedure of the heart), and that such modules would include additional class and features modules therein. In addition, for non-imaging types of medical equipment, e.g., an EKG machine, labeling modules may also be provided to classify the output of the EKG machine into one or more classes (e.g., heart rate anomalies, QT interval anomalies, R-wave anomalies, etc.) having different structures and analytical processes but a similar purpose of classifying the equipment output into one or more classes.

Applicants have discovered that the automated capture and labeling of reference image data sets may be improved by automatically adjusting certain parameters within the feature modules 715, 720, 725, etc. As previously noted, the features modules use standard image processing algorithms to determine whether the defined features are present in each image. These image processing algorithms in the feature modules (e.g., color analysis algorithms, thresholding algorithms, convolution with kernels, contour detection and segmentation, clustering and distance measurements) include a number of parameters that are usually maintained as constants, but which may be adjusted. Applicants have discovered that by automatically optimizing these adjustable parameters within the image processing algorithms using Particle Swarm Optimization, it is possible to minimize the number of mislabeled images by the image processing algorithms in the features modules. Automatic adjustment of the feature modules analysis image processing algorithms is discussed more fully in connection with FIG. 8.

Figure 8:
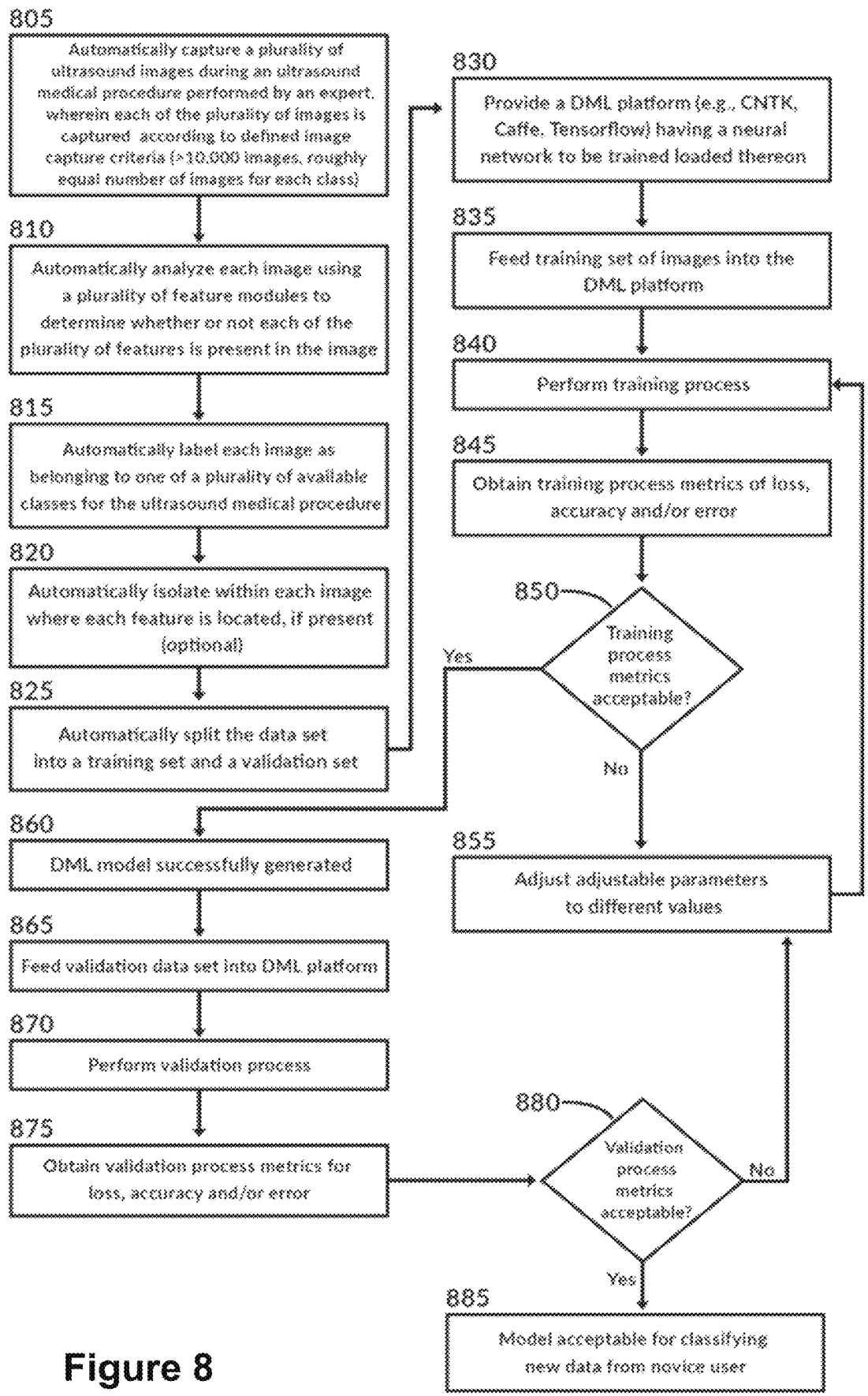
FIG. 8 is a flowchart of a method for developing a machine learning module using automatically prepared data sets.

FIG. 8 illustrates one embodiment of a method 802 for developing a machine learning (ML) model of a neural network for classifying images for a medical procedure using automatically prepared data sets for an ultrasound system. In one embodiment, the method may be performed using a system according to FIG. 1 that incorporates the machine learning development module (MLDM) 705 of FIG. 7. In alternative embodiments, the method may be implemented for different types of medical or non-medical equipment.

The method includes automatically capturing a plurality of ultrasound images (805) during a reference ultrasound procedure (e.g., performed by an expert), wherein each of the plurality of images is captured according to defined image capture criteria. In one embodiment, capture may be performed by an image capture module implemented in a computer (e.g., computer 700, FIG. 1) in one or more of software, firmware, or hardware, such as image capture module 710 and GUI 712 (FIG. 7).

Referring again to FIG. 8, the method further comprises automatically analyzing each image to determine whether one or more features is present in each image (810). The features correspond to those present in one or more image classes, and the presence or absence of certain features may be used to classify a given image in one or more image classes for the reference medical procedure. A plurality of feature modules (e.g., feature modules 715, 720, etc. of FIG. 7) stored in a memory may be used to analyze the images for the presence or absence of each feature. The feature modules may comprise software, firmware, or hardware, and a computer such as computer 700 of FIG. 1 may analyze image captured image using the feature modules.

The method further comprises automatically classifying and labeling (815) each image as belonging to one of a plurality of available classes for the ultrasound medical procedure. As noted above, each image may be assigned to a class based on the features present or absent from the image. After an image is classified, the method further comprises labeling the image with its class. Labeling may be performed by storing in memory the image's class, or otherwise associating the result of the classification process with the image in a computer memory. In one embodiment, image classification may be performed by a classification module such as classification module 750 of FIG. 7. Labeling may be performed by the classification module that classifies the image, or by a separate labeling module.

In some embodiments, the method may also involve automatically isolating (e.g., using boxes, circles, highlighting or other designation) within each image where each feature (i.e., those determined to be present in the feature analysis step) is located within the image (820). This step is optional and may not be performed in some embodiments. In one embodiment, automatic feature isolation (or bounding) may be performed by an isolation module that determines the boundary of each feature based on the characteristics that define the feature. The isolation module may apply appropriate boundary indicators (e.g., boxes, circles, ellipses, etc.) as defined in the isolation module, which in some embodiments may allow a user to select the type of boundary indicator to be applied.

After the images have been classified and labeled, the method includes automatically splitting the set of labeled images into a training set and a validation set (825). The training set preferably is larger than the validation set (i.e., comprises more than 50% of the total images in the data set), and may range from 70-90%, more preferably 80-85%, of the total images. Conversely, the validation set may comprise from 10-30, more preferably from 15-20%, of the total images.

The remaining steps in the method 802 (e.g., steps 830-885) are automated steps that are similar to corresponding steps 630-685 and which, for brevity, are described in abbreviated form. The method further comprises providing a Deep Machine Learning (DML) platform (e.g., CNTK, Caffe, or Tensorflow) having a neural network to be trained loaded onto it (830). More specifically, a neural network (e.g., ResNet) is provided as a program in a computer language such as NDL or Python in the DML platform.

The training set is fed into the DML platform (835) and the training process is performed (840). The training process comprises iteratively computing weights and biases for the nodes of the neural network using feed-forward and back-propagation, as previously described, until the accuracy of the network in classifying images reaches an acceptable threshold level of accuracy.

The training process metrics of loss, accuracy, and/or error are obtained (845) at the conclusion of the training process, and a determination is made (850) whether the training process metrics are within an acceptable threshold for each metric. If the training process metrics are unacceptable, the adjustable parameters of the DML platform (and optionally those of the neural network) are adjusted to different values (855) and the training process is restarted (840). In one example involving CNTK as the DML platform, the tunable or adjustable parameters include learning rate constraints, number of epochs to train, epoch size, minibatch size, and momentum constraints.

The training process may be repeated one or more times if error metrics are not acceptable, with new adjustable parameters being provided each time the training process is performed. In one embodiment, if the error metrics obtained for the training process are unacceptable, adjustments to the adjustable parameters (855) of the DML platform are made automatically, using an optimization technique such as Particle Swarm Optimization. Additional details on particle swarm theory are provided by Eberhart, R. C. & Kennedy, J., "A New Optimizer Using Particle Swarm Theory," Proceedings of the Sixth International Symposium on Micro Machine and Human Science, 39-43 (1995). In another embodiment, adjustments to the adjustable parameters (855) in the event of unacceptable error metrics are made manually by a designer.

In one embodiment, each time automatic adjustments are made (855) to the adjustable parameters of the DML platform, automatic adjustments are also made to the adjustable parameters of the image processing algorithms used in the feature modules. As discussed in connection with FIG. 7, standard image processing algorithms (e.g., color analysis algorithms, thresholding algorithms, convolution with kernels, contour detection and segmentation, clustering and distance measurements) include a number of parameters that are usually maintained as constants, but which may be adjusted. In a particular embodiment, the step of adjusting the adjustable parameters of the DML platform comprises automatically adjusting at least one of the adjustable parameters of the DML platform and automatically adjusting at least one of the adjustable parameters of the image processing algorithms. In a still more specific embodiment, Particle Swarm Optimization is used to automatically adjust both at least one adjustable parameter of the DML platform and at least one adjustable parameter of an image processing algorithm.

If the training process 840 fails to yield acceptable metrics (650) after a specific number of iterations (which may be manually determined, or automatically determined by, e.g., Particle Swarm Optimization), then the data set is insufficient to properly train the neural network and the data set is regenerated. If the metrics are within an acceptable threshold for each metric, then a DML model has been successfully generated (860). In one embodiment, acceptable error metrics may range from less than 5% to less than 10% average cross-entropy error for all epochs, and from less than 50% to less than 10% average classification error for all epochs. If will be recognized that different development projects may involve different acceptable thresholds, and that different DML platforms may use different types of error metrics.

If a successful DML model is generated (860), the method then includes feeding the validation data set to the DML model (865), and the validation process is performed (870) using the validation data set. After the completion of the validation process, validation process metrics for loss, accuracy and/or error are obtained (875) for the validation process.

A determination is made (880) whether the validation metrics are within an acceptable threshold for each metric, which may be the same as or different from those used for the training process. If the validation process metrics are outside of the acceptable threshold, the adjustable parameters are adjusted to different values (855) and the training process is restarted (840). If the metrics are acceptable, then the DML model may be used to classify new data (885). In one embodiment, the step of adjusting the adjustable parameters of the DML platform after the validation process comprises automatically adjusting at least one of the adjustable parameters of the DML platform and automatically adjusting at least one of the adjustable parameters of the image processing algorithms, for example by an algorithm using Particle Swarm Optimization.

The process may be allowed to continue through one or more additional cycles. If evaluation process metrics are still unacceptable, then the data set is insufficient to properly train the neural network, and the data set needs to be regenerated.

Figure 9A:
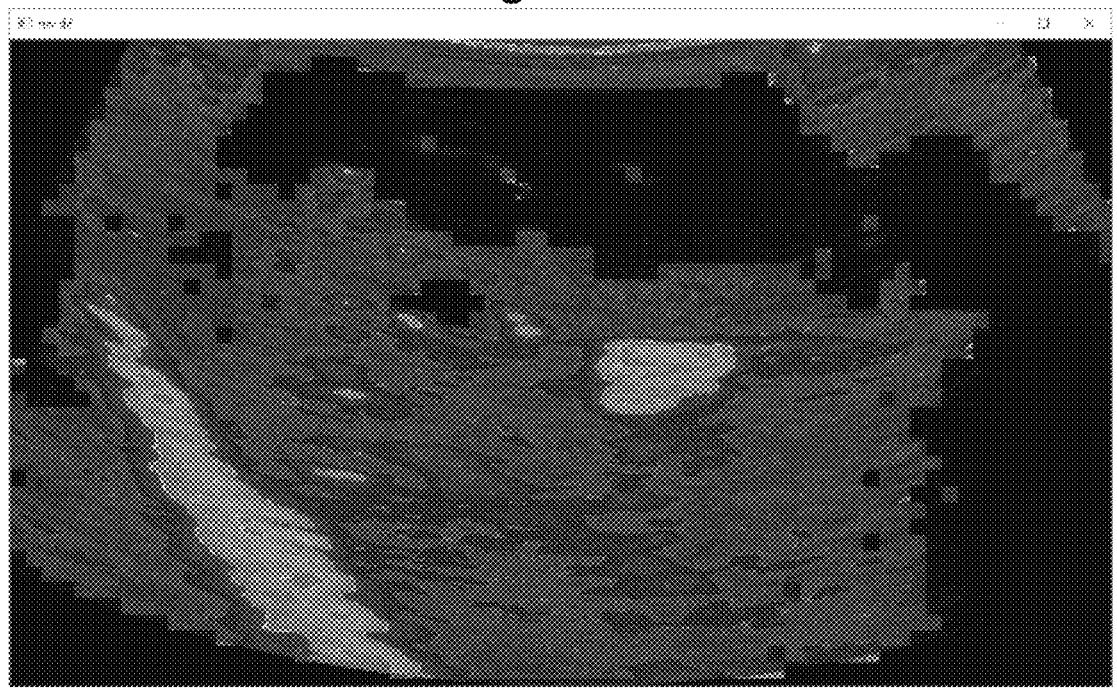
FIGS. 9A-9F are ultrasound images that illustrate one or more features that may be used to classify ultrasound images.
Figure 9B:
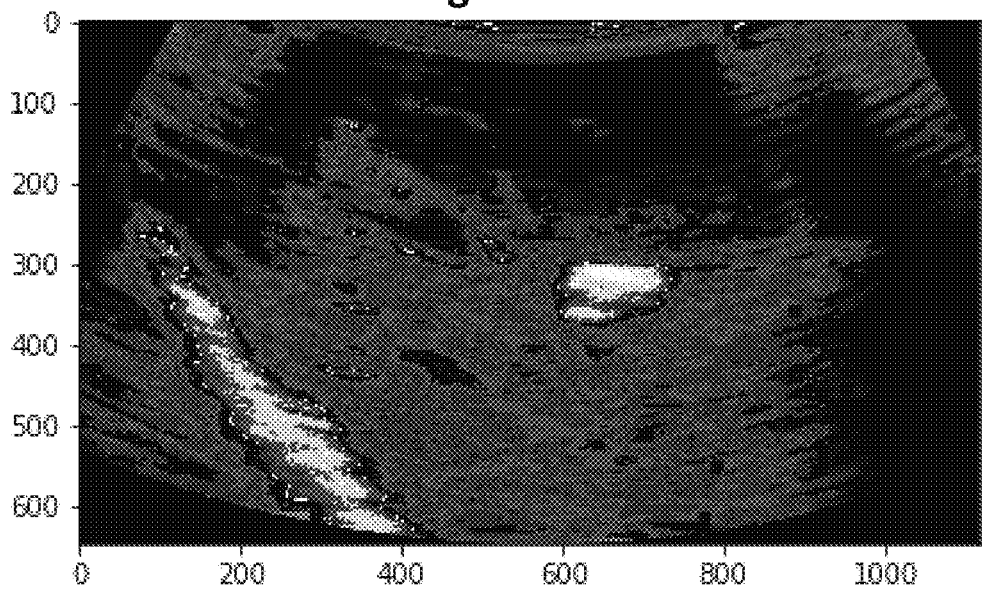

FIGS. 9A-9G are examples of features that may be used to classify images into the class of "radial cross section of the carotid artery." In some embodiments, ultrasound systems capable of providing color data may be used, and systems of the present invention may provide outcome-based feedback from color data in captured images. Although rendered in grayscale for simplicity, FIGS. 9A and 9B illustrates an image of a carotid artery processed to identify colors using the HSV color space, although in alternative embodiments color may be represented as values in other color space schemes such as RGB. Persons of skill in the art of processing color ultrasound images will appreciate that bright color intensity in several areas suggests the presence of blood flow, especially in the lighter blue and lighter turquoise areas (FIG. 9A) and the white areas (FIG. 9B) of the V channel of the HSV color space. In alternative embodiments, ultrasound systems capable of only grayscale images may be used.

Figure 9C:
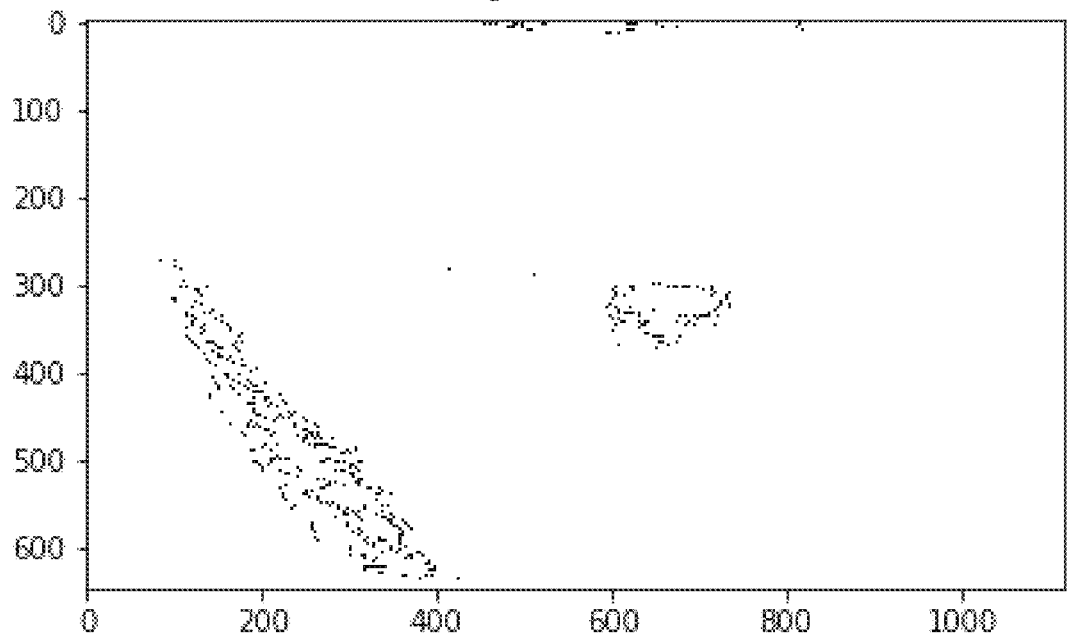

FIG. 9C was obtained by processing the image of FIG. 9A using adapted thresholding and Canny edge detection to identify the general contour of the arterial wall, with the contours being represented as edges in a graphical figure. FIG. 9C illustrates a generally circular area in the center-right area of the figure that suggests the possibility of a radial cross-section of the carotid artery. A linear area on the lower left suggests the possibility of bright artifacts that are of little interest.

Figure 9D:
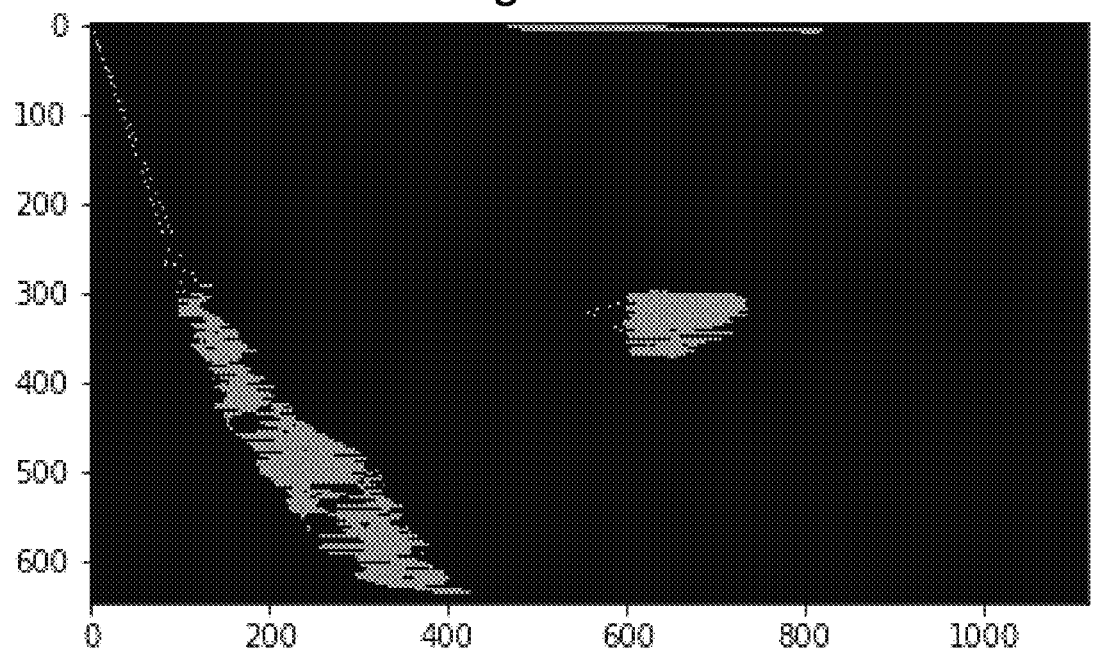

FIG. 9D was obtained by processing the image of FIG. 9A using clustering to identify clusters of contours, and isolate the single cluster of contours that match the general area of the lumen of the artery. The generally elliptical area in the center-right is the single cluster of contours that match the general area and geometry of the radial cross section of the carotid artery, while the three clusters are merely artifacts or noise that do not match the general area or geometry of the aforementioned cross section.

Figure 9E:
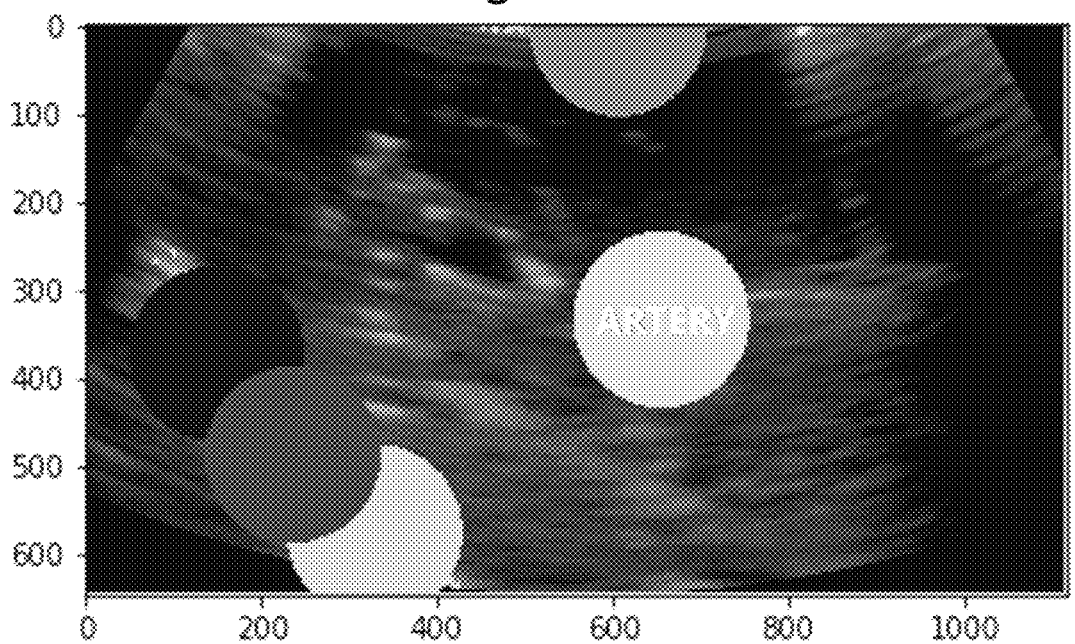

FIG. 9E is a generalization of FIG. 9D using the centers of mass for each cluster to show how clusters are expected to be positioned relative to each other. The clusters are represented as sets of points in 2D space. Proximity is represented as vectors.

Figure 9F:
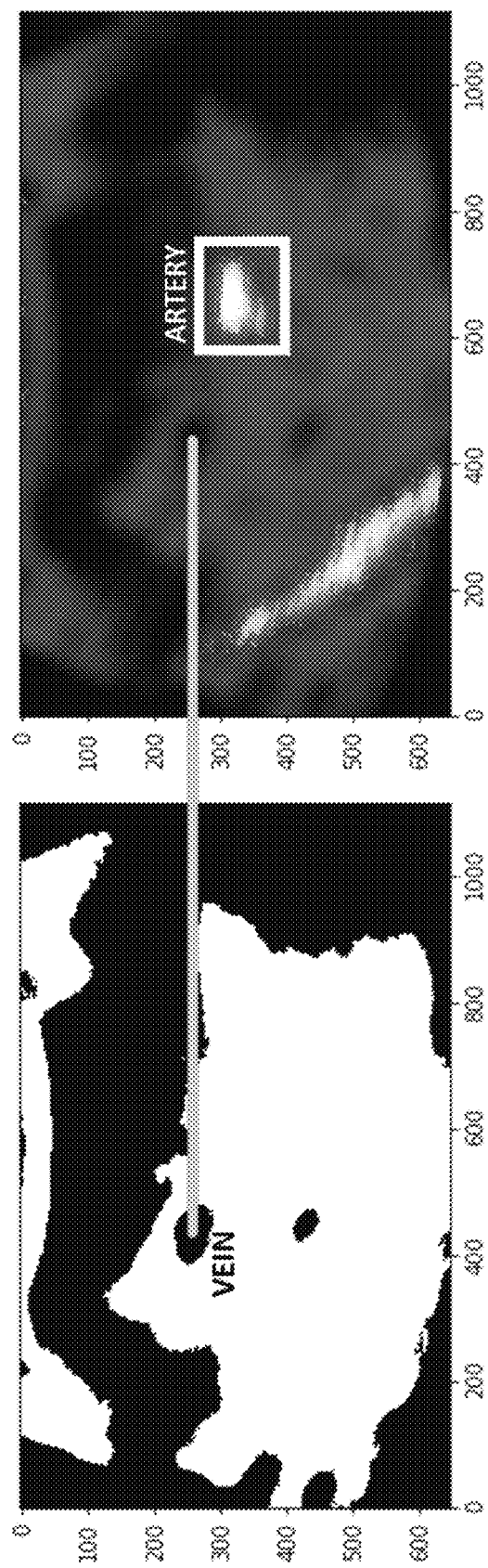

FIG. 9F uses known anatomical markers, such as cross sections of veins or bones, and expected relative positions to verify structures. In particular, the right-side portion of FIG. 9F shows the bright radial cross section of the carotid artery as processed in FIG. 9B, and is compared to the left-side portion of FIG. 9F, which shows the same image processed using binary thresholding to better illustrate (upper dark elliptical region in large white area) where the nearby jugular vein would be. This illustrates the expected proximity of the artery relative to the vein, and confirms the position of the artery shown in FIG. 9E.

As discussed in connection with FIGS. 6 and 8, preparation of the images for the neural network training and validation data sets in some embodiments includes isolating or visually indicating in the images where features are located. Isolating involves applying boundary indicators, such as a bounding box, circle, ellipse, or other regular or irregular bounding shape or region, around the feature of interest. In one embodiment (FIG. 6, step 820) this optional step may be performed manually by an expert as part of the manual process of preparing the data sets for training the neural network. In another embodiment (FIG. 8, step 820), automatic feature isolation (or bounding) may be performed automatically by an isolation module that determines the boundary of each feature based on the characteristics that define the feature.

Figure 10A:
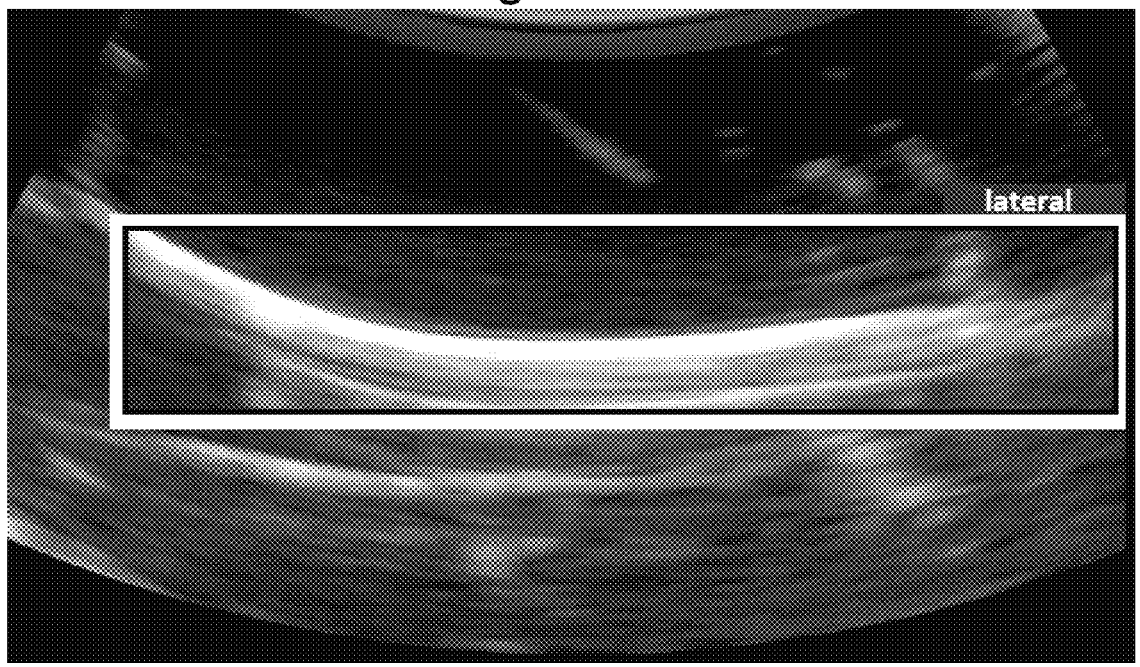
FIGS. 10A and 10B are ultrasound images illustrating isolating or labeling specific structures in each image.
Figure 10B:
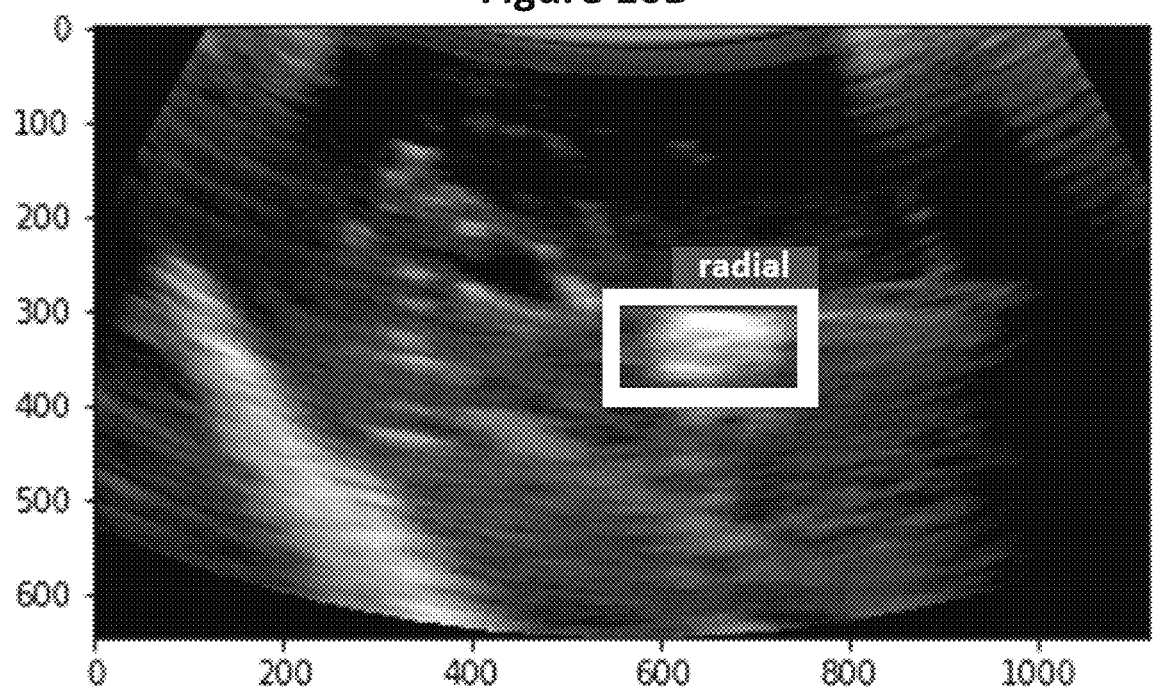

Examples of isolating boxes are shown in FIGS. 10A and 10B. FIG. 10A shows a manually generated bounding box to indicate the presence of a lateral view of a carotid artery. FIG. 10B illustrates a manually generated bounding box to indicate the presence of a cross-sectional view of a carotid artery.

In various embodiments, the present invention relates to the subject matter of the following numbered paragraphs.

101. A method for providing real-time, three-dimensional (3D) augmented reality (AR) feedback guidance to a user of a medical equipment system, the method comprising:

receiving data from a medical equipment system during a medical procedure performed by a user of the medical equipment to achieve a medical procedure outcome;

sensing real-time user positioning data relating to one or more of the movement, position, and orientation of at least a portion of the medical equipment system within a volume of the user's environment during the medical procedure performed by the user;

retrieving from a library at least one of 1) stored reference positioning data relating to one or more of the movement, position, and orientation of at least a portion of the medical equipment system during reference a medical procedure, and 2) stored reference outcome data relating to a reference performance of the medical procedure;

comparing at least one of 1) the sensed real-time user positioning data to the retrieved reference positioning data, and 2) the data received from the medical equipment system during a medical procedure performed by the user to the retrieved reference outcome data;

generating at least one of 1) real-time position-based 3D AR feedback based on the comparison of the sensed real-time user positioning data to the retrieved reference positioning data, and 2) real-time outcome-based 3D AR feedback based on the comparison of the data received from the medical equipment system during a medical procedure performed by the user to the retrieved reference outcome data; and providing at least one of the real-time position-based 3D AR feedback and the real-time outcome-based 3D AR feedback to the user via an augmented reality user interface (ARUI).

102. The method of claim 101, wherein the medical procedure performed by a user of the medical equipment comprises a first medical procedure, and the stored reference positioning data and stored reference outcome data relate to a reference performance of the first medical procedure prior to the user's performance of the first medical procedure.

103. The method of claim 101, wherein the medical procedure performed by a user of the medical equipment comprises a first ultrasound procedure, and the stored reference positioning data and stored reference outcome data comprise ultrasound images obtained during a reference performance of the first ultrasound procedure prior to the user's performance of the first ultrasound procedure.

104. The method of claim 103, wherein sensing real-time user positioning data comprises sensing real-time movement by the user of an ultrasound probe relative to the body of a patient.

105. The method of claim 101, wherein generating real-time outcome-based 3D AR feedback is based on a comparison, using a neural network, of real-time images generated by the user in an ultrasound procedure to retrieved images generated during a reference performance of the same ultrasound procedure prior to the user.

106. The method of claim 105, wherein the comparison is performed by a convolutional neural network.

107. The method of claim 101, wherein sensing real-time user positioning data comprises sensing one or more of the movement, position, and orientation of at least a portion of the medical equipment system by the user with a sensor comprising at least one of a magnetic GPS system, a digital camera tracking system, an infrared camera system, an accelerometer, and a gyroscope.

108. The method of claim 101, wherein sensing real-time user positioning data comprises sensing at least one of:

a magnetic field generated by said at least a portion of the medical equipment system;

the movement of one or more passive visual markers coupled to one or more of the patient, a hand of the user, or a portion of the medical equipment system; and the movement of one or more active visual markers coupled to one or more of the patient, a hand of the user, or a portion of the medical equipment system.

109. The method of claim 101, wherein providing at least one of the real-time position-based 3D AR feedback and the real-time outcome-based 3D AR feedback to the user comprises providing a feedback selected from:

a virtual prompt indicating a movement correction to be performed by a user;

a virtual image or video instructing the user to change the orientation of a probe to match a desired orientation;

a virtual image or video of a correct motion path to be taken by the user in performing a medical procedure;

a color-coded image or video indicating correct and incorrect portions of the user's motion in performing a medical procedure;

and instruction to a user to press an ultrasound probe deeper or shallower into tissue to focus the ultrasound image on a desired target structure of the patient's body;

an auditory instruction, virtual image, or virtual video indicating a direction for the user to move an ultrasound probe; and tactile information.

110. The method of claim 101, wherein providing at least one of the real-time position-based 3D AR feedback and the real-time outcome-based 3D AR feedback comprises providing both of the real-time position-based 3D AR feedback and the real-time outcome-based 3D AR feedback to the user.

111. The method of claim 101, wherein providing at least one of the real-time position-based 3D AR feedback and the real-time outcome-based 3D AR feedback comprises providing said at least one feedback to a head mounted display (HMD) worn by the user.

201. A method for developing a machine learning model of a neural network for classifying images for a medical procedure using an ultrasound system, the method comprising:

A) performing a first medical procedure using an ultrasound system;

B) automatically capturing a plurality of ultrasound images during the performance of the first medical procedure, wherein each of the plurality of ultrasound images is captured at a defined sampling rate according to defined image capture criteria;

C) providing a plurality of feature modules, wherein each feature module defines a feature which may be present in an image captured during the medical procedure;

D) automatically analyzing each image using the plurality of feature modules;

E) automatically determining, for each image, whether or not each of the plurality of features is present in the image, based on the analysis of each imagine using the feature modules;

F) automatically labeling each image as belonging to one class of a plurality of image classes associated with the medical procedure;

G) automatically splitting the plurality of images into a training set of images and a validation set of images;

H) providing a deep machine learning (DML) platform having a neural network to be trained loaded thereon, the DML platform having a plurality of adjustable parameters for controlling the outcome of a training process;

I) feeding the training set of images into the DML platform;

J) performing the training process for the neural network to generate a machine learning model of the neural network;

K) obtaining training process metrics of the ability of the generated machine learning model to classify images during the training process, wherein the training process metrics comprise at least one of a loss metric, an accuracy metric, and an error metric for the training process;

L) determining whether each of the at least one training process metrics is within an acceptable threshold for each training process metric;

M) if one or more of the training process metrics are not within an acceptable threshold, adjusting one or more of the plurality of adjustable DML parameters and repeating steps J, K, and L;

N) if each of the training process metrics is within an acceptable threshold for each metric, performing a validation process using the validation set of images;

O) obtaining validation process metrics of the ability of the generated machine learning model to classify images during the validation process, wherein the validation process metrics comprise at least one of a loss metric, an accuracy metric, and an error metric for the validation process;

P) determining whether each of the validation process metrics is within an acceptable threshold for each validation process metric;

Q) if one or more of the validation process metrics are not within an acceptable threshold, adjusting one or more of the plurality of adjustable DML parameters and repeating steps J-P; and R) if each of the validation process metrics is within an acceptable threshold for each metric, storing the machine learning model for the neural network.

202. The method of claim 201, further comprising:

S) receiving, after storing the machine learning model for the neural network, a plurality of images from a user performing the first medical procedure using an ultrasound system;

T) using the stored machine learning model to classify each of the plurality of images received from the ultrasound system during the second medical procedure.

203. The method of claim 201, further comprising:

S) using the stored machine learning model for the neural network to classify a plurality of ultrasound images for a user performing the first medical procedure.

204. The method of claim 201, wherein performing the training process comprises iteratively computing weights and biases for each of the nodes of the neural network using feed-forward and back-propagation until the accuracy of the network in classifying images reaches an acceptable threshold level of accuracy.

205. The method of claim 201, wherein performing the validation process comprises using the machine learning model generated by the training process to classify the images of the validation set of image data.

206. The method of claim 201, further comprising stopping the method if steps J, K, and L have been repeated more than a threshold number of repetitions.

207. The method of claim 206, further comprises stopping the method if steps N-Q have been repeated more than a threshold number of repetitions.

208. The method of claim 201, wherein providing a deep machine learning (DML) platform comprises providing a DML platform having at least one adjustable parameter selected from learning rate constraints, number of epochs to train, epoch size, minibatch size, and momentum constraints.

209. The method of claim 208, wherein adjusting one or more of the plurality of adjustable DML parameters comprises automatically adjusting said one or more parameters using a particle swarm optimization algorithm.

210. The method of claim 201, wherein automatically splitting the plurality of images comprises automatically splitting the plurality of images into a training set comprising from 70% to 90% of the plurality of images, and a validation set comprising from 10% to 30% of the plurality of images.

211. The method of claim 201, wherein automatically labeling each image further comprises isolating one or more of the features present in the image using a boundary indicator selected from a bounding box, a bounding circle, a bounding ellipse, and an irregular bounding region.

212. The method of claim 201, wherein obtaining training process metrics comprises obtaining at least one of average cross-entropy error for all epochs and average classification error for all epochs.

213. The method of claim 201, wherein determining whether each of the training process metrics are within an acceptable threshold comprises determining whether average cross-entropy error for all epochs is less than a threshold selected from 5% to 10%, and average classification error for all epochs is less than a threshold selected from 15% to 10%.

214. The method of claim 201, wherein step A) is performed by an expert.

The particular embodiments disclosed above are illustrative only, as the invention may be modified and practiced in different but equivalent manners apparent to those skilled in the art having the benefit of the teachings herein. Examples are all intended to be non-limiting. Furthermore, exemplary details of construction or design herein shown are not intended to limit or preclude other designs achieving the same function. It is therefore evident that the particular embodiments disclosed above may be altered or modified and all such variations are considered within the scope and spirit of the invention, which are limited only by the scope of the claims.

Embodiments of the present invention disclosed and claimed herein may be made and executed without undue experimentation with the benefit of the present disclosure. While the invention has been described in terms of particular embodiments, it will be apparent to those of skill in the art that variations may be applied to systems and apparatus described herein without departing from the concept, spirit and scope of the invention.

What is claimed is:

1. A method for developing a machine learning model of a neural network for classifying images for a medical procedure using an ultrasound system, the method comprising:
    A) performing a first medical procedure using an ultrasound system;
    B) automatically capturing a plurality of ultrasound images during the performance of the first medical procedure, wherein each of the plurality of ultrasound images is captured at a defined sampling rate according to defined image capture criteria;
    C) providing a plurality of feature modules, wherein each feature module defines a feature which may be present in an image captured during the medical procedure;
    D) automatically analyzing each image using the plurality of feature modules;
    E) automatically determining, for each image, whether or not each of the plurality of features is present in the image, based on the analysis of each imagine using the feature modules;
    F) automatically labeling each image as belonging to one class of a plurality of image classes associated with the medical procedure;
    G) automatically splitting the plurality of images into a training set of images and a validation set of images;
    H) providing a deep machine learning (DML) platform having a neural network to be trained loaded thereon, the DML platform having a plurality of adjustable parameters for controlling the outcome of a training process;
    I) feeding the training set of images into the DML platform;
    J) performing the training process for the neural network to generate a machine learning model of the neural network;
    K) obtaining training process metrics of the ability of the generated machine learning model to classify images during the training process, wherein the training process metrics comprise at least one of a loss metric, an accuracy metric, and an error metric for the training process;
    L) determining whether each of the at least one training process metrics is within an acceptable threshold for the training process metric;
    M) if one or more of the training process metrics are not within an acceptable threshold, adjusting one or more of the plurality of adjustable DML parameters and repeating steps J, K, and L using the training set of images;
    N) if each of the training process metrics is within an acceptable threshold for the metric, performing a validation process using the validation set of images;
    O) for each validation process performed in step N;
        1) obtaining validation process metrics of the ability of the generated machine learning model to classify images during the validation process, wherein the validation process metrics comprise at least one of a loss metric, an accuracy metric, and an error metric for the validation process;
        2) determining whether each of the validation process metrics is within an acceptable threshold for the validation process metric;
        3) if one or more of the validation process metrics are not within an acceptable threshold, adjusting one or more of the plurality of adjustable DML parameters and repeating steps J-O(2); and 4) if each of the validation process metrics is within an acceptable threshold for each metric, storing the machine learning model for the neural network.

2. The method of claim 1, further comprising:
P) after each machine learning model storing performed in step O(4),
1) receiving a plurality of images from a user performing the first medical procedure using an ultrasound system;
2) using the stored machine learning model to classify each of the plurality of images received from the ultrasound system during step P(1).

3. The method of claim 1, further comprising:
P) after each machine learning model storing performed in step O(4), using the stored machine learning model for the neural network to classify a plurality of ultrasound images for a user performing the first medical procedure.

4. The method of claim 1, wherein the neural network comprises a plurality of nodes, and wherein performing the training process comprises iteratively computing weights and biases for each of the nodes of the neural network using feed-forward and back-propagation until the accuracy of the network in classifying images reaches an acceptable threshold level of accuracy.

5. The method of claim 1, wherein each validation process performed in step N comprises using the machine learning model generated by the training process to classify the images of the validation set of image data.

6. The method of claim 1, wherein the plurality of images comprises a data set, the method further comprising regenerating the data set if steps J, K, and L have been repeated more than a threshold number of repetitions.

7. The method of claim 6, further comprises restarting the method if steps N-Q have been repeated more than a threshold number of repetitions.

8. The method of claim 1, wherein providing a deep machine learning (DML) platform comprises providing a DML platform having at least one adjustable parameter selected from learning rate constraints, number of epochs to train, epoch size, minibatch size, and momentum constraints.

9. The method of claim 8, wherein adjusting one or more of the plurality of adjustable DML parameters comprises automatically adjusting said one or more parameters using a particle swarm optimization algorithm.

10. The method of claim 1, wherein automatically splitting the plurality of images comprises automatically splitting the plurality of images into a training set comprising from 70% to 90% of the plurality of images, and a validation set comprising from 10% to 30% of the plurality of images.

11. The method of claim 1, wherein automatically labeling each image further comprises isolating one or more of the features present in the image using a boundary indicator selected from a bounding box, a bounding circle, a bounding ellipse, and an irregular bounding region.

12. The method of claim 1, wherein obtaining training process metrics comprises obtaining at least one of average cross-entropy error for all training epochs and average classification error for all training epochs.

13. The method of claim 1, wherein determining whether each of the training process metrics are within an acceptable threshold comprises determining whether average cross-entropy error for all training epochs is less than a threshold selected from 5% to 10%, and average classification error for all training epochs is less than a threshold selected from 15% to 10%.

14. The method of claim 1, wherein step A) is performed by an expert.

15. A method for developing a machine learning model of a neural network for classifying images for a medical procedure using a medical imaging system, the method comprising:
A) performing a first medical procedure using an imaging system;
B) capturing a plurality of images during the performance of the first medical procedure;
C) providing a plurality of feature modules, each feature module defining a feature which may be present in an image captured during the medical procedure;
D) automatically analyzing each image using the plurality of feature modules;
E) automatically determining, for each image, whether or not each of the plurality of features is present in the image, based on the analysis of each imagine using the feature modules;
F) labeling each image as belonging to one class of a plurality of image classes associated with the medical procedure;
G) automatically splitting the plurality of images into a training set of images and a validation set of images;
H) providing a deep machine learning (DML) platform having a neural network to be trained loaded thereon, the DML platform having a plurality of adjustable parameters for controlling the outcome of a training process;
I) feeding the training set of images into the DML platform;
J) performing the training process for the neural network to generate a machine learning model of the neural network;
K) obtaining training process metrics of the ability of the generated machine learning model to classify images during the training process, wherein the training process metrics comprise at least one of a loss metric, an accuracy metric, and an error metric for the training process;
L) determining whether each of the at least one training process metrics is within an acceptable threshold for the training process metric;
M) if one or more of the training process metrics are not within an acceptable threshold, adjusting one or more of the plurality of adjustable DML parameters and repeating steps J, K, and L using the training set of images;
N) if each of the training process metrics is within an acceptable threshold for the metric, performing a validation process using the validation set of images;
O) for each validation process performed in step N;
1) obtaining validation process metrics of the ability of the generated machine learning model to classify images during the validation process, wherein the validation process metrics comprise at least one of a loss metric, an accuracy metric, and an error metric for the validation process;
2) determining whether each of the validation process metrics is within an acceptable threshold for the validation process metric;
3) if one or more of the validation process metrics are not within an acceptable threshold, adjusting one or more of the plurality of adjustable DML parameters and repeating steps J-O(2); and 4) if each of the validation process metrics is within an acceptable threshold for each metric, storing the machine learning model for the neural network.

16. The method of claim 15, wherein capturing a plurality of images during the performance of the first medical procedure comprises automatically capturing images at a defined sampling rate according to defined image capture criteria.

17. The method of claim 15, further comprising:
P) after each machine learning model storing performed in step O(4), using the stored machine learning model for the neural network to classify a plurality of images captured by a user of the imaging system during the performance of the first medical procedure.

18. The method of claim 15, wherein the neural network comprises a plurality of nodes, and wherein performing the training process comprises iteratively computing weights and biases for each of the nodes of the neural network using feed-forward and back-propagation until the accuracy of the network in classifying images reaches an acceptable threshold level of accuracy.

19. The method of claim 15, wherein the imaging system is an ultrasound imaging system.

20. The method of claim 15, wherein labeling each image as belonging to one class of a plurality of image classes associated with the medical procedure comprises automatically labeling each image.

* * * * *